US009549951B2

(12) United States Patent
Brown et al.

(10) Patent No.: US 9,549,951 B2
(45) Date of Patent: *Jan. 24, 2017

(54) REACTIVE OXIDATIVE SPECIES GENERATING MATERIALS AND METHODS OF USE

(71) Applicant: W. L. Gore & Associates, Inc., Newark, DE (US)

(72) Inventors: Tiffany J. Brown, Landenberg, PA (US); Adam S. Lafleur, Norwood, MA (US); Kenneth Mazich, Birmingham, MI (US); Jeffrey C. Towler, Wilmington, DE (US); Ji Zhang, Newark, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/993,324

(22) Filed: Jan. 12, 2016

(65) Prior Publication Data

US 2016/0120904 A1    May 5, 2016

Related U.S. Application Data

(62) Division of application No. 14/013,117, filed on Aug. 29, 2013, now Pat. No. 9,259,435.

(60) Provisional application No. 61/695,432, filed on Aug. 31, 2012.

(51) Int. Cl.
| | | |
|---|---|---|
| *A61K 31/765* | (2006.01) | |
| *A61K 33/40* | (2006.01) | |
| *A61L 27/34* | (2006.01) | |
| *A61L 27/50* | (2006.01) | |
| *A61L 27/58* | (2006.01) | |
| *A61L 2/08* | (2006.01) | |

(52) U.S. Cl.
CPC ............. *A61K 33/40* (2013.01); *A61K 31/765* (2013.01); *A61L 27/34* (2013.01); *A61L 27/50* (2013.01); *A61L 27/58* (2013.01); *A61L 2/081* (2013.01); *A61L 2/087* (2013.01)

(58) Field of Classification Search
CPC .......... A61L 27/34; A61L 27/50; A61L 27/58; A61L 2/081; A61L 2/087; C08L 67/04; A61K 31/765; A61K 33/40
See application file for complete search history.

(56) References Cited

U.S. PATENT DOCUMENTS

| | | | |
|---|---|---|---|
| 4,243,775 A | | 1/1981 | Rosensaft et al. |
| 5,376,716 A | * | 12/1994 | Nayak ..................... C08K 5/12 524/295 |
| 6,103,275 A | | 8/2000 | Seitz et al. |
| 6,165,217 A | * | 12/2000 | Hayes .................. A61L 31/06 428/36.4 |
| 6,383,750 B1 | | 5/2002 | Guillet et al. |
| 2004/0184956 A1 | * | 9/2004 | Steklenski ................ G01T 1/04 436/58 |
| 2007/0203564 A1 | | 8/2007 | Rusk et al. |
| 2008/0101982 A1 | | 5/2008 | Comolli et al. |
| 2009/0264490 A1 | | 10/2009 | Zanella et al. |
| 2011/0280919 A1 | | 11/2011 | Moloye-Olabisi et al. |
| 2012/0024196 A1 | | 2/2012 | Markou |

FOREIGN PATENT DOCUMENTS

| | | |
|---|---|---|
| WO | WO2008-095148 | 8/2008 |
| WO | WO2012/024196 | 2/2012 |

OTHER PUBLICATIONS

Ali et al. (Biomaterials 1993, vol. 14 No. 9 pp. 648-655).*
Mader et al., Gamma-sterilization-induced Radicals in Biodegradable Drug Delivery Systems, Appl.Radiat.Isot., vol. 47, No. 11/12, 1996, pp. 1669-1674.
Nishikawa et al., Oxidative Stress and Cancer Therapy, Journal of Clinical and Experimental Medicine, vol. 214, No. 11, 2005, pp. 953-956.
Dorati et al., γ Irradiation of PEGd,lPLA and PEG-PLGA Multiblock Copolymers: I. Effect of Irradiation Doses, AAPS PharmSciTech, vol. 9, No. 2, Jun. 2008, pp. 718-725.
Ali, Mechanisms of polymer degradation in implantable devices, Biomaterials, Jul. 1993, vol. 14, No. 9, pp. 648-656.
Bancirova, Sodium Azide as a Specific Quencher of Singlet Oxygen During Chemiluminescent Detection by Luminol and Cyprindia Luciferin Analogues, Luminescence, 2011, p. 685-88.
Chen, Senescence-like Growth Arrest Induced by Hydrogen Perioxide in Human Diploid Fibroblast F65 Cells, Cell Biology, 1994, 91(10), p. 4130-34.
Couffinhal, Impaired Collateral Vessel Development Associated with Reduced Expression of Vascular Endothelial Growth Factor in ApoE Mice, American Heart Association Circulation, 1999, p. 3188-98.
D'Autreaux, ROS as Signalling Molecules, Nature Reviews/Molecular Cell Biology, 2007, p. 813-824.
Deshpande, Mechanism of Hydrogen Peroxide-Induced Cell Cycle Arrest in Vascular Smooth Muscle, Antioxidants and Rdox Signaling, vol. 4, No. 5, 2002, p. 845-54.
Dolmans, Photodynamic Therapy for Cancer, Nature Publishing Group, vol. 3, 2003, p. 380-7.
Eaton, Quantitative EPR, 2010, p. 30-32, 3 pages.
Klebanoff, Oxygen Metabolism, 1980, 93, p. 480-9.
Kohanski, Common Mechanism of Cell, 2007, p. 797-810, vol. 130.
Krotz, Arteriosclerosis, Thrombosis, and Vascular Biology, Jrl of the American Heart Assoc., 2004, p. 1988-96.

(Continued)

Primary Examiner — Anna Falkowitz
(74) Attorney, Agent, or Firm — Amy L. Miller

(57) ABSTRACT

Materials capable of delivering stabilized free radicals to targeted treatment sites. The materials comprise semi-crystalline, hydrolytically degradable polymers that are subjected to ionizing radiation to create stabilized free radicals therein. Upon exposure to oxygen containing aqueous media, the materials generate reactive oxidative species which are useful in biological processes.

12 Claims, 23 Drawing Sheets

(56) References Cited

OTHER PUBLICATIONS

Li, Hydrogen Peroxide Induces G2 Cell Cycle Arrest and Inhibits Cell Proliferation in Osteoblasts, Anatomical Record, 2009, p. 1107-13.
Rao, Active oxygen species stimulate vascular smooth muscle cell growth and proto-oncogene expression, Circulation Research, Mar. 1992, vol. 70, No. 3, pp. 593-599.
Silva, Effects of VEGF temporal and spatial presentation on angiogenesis, Biomaterials, 2009, 31(6), p. 1235-41.
Turrens, Mitochondria Formation, Jr. Physiol 2003, p. 335-344, vol. 552 (2).
Veal, Hydrogen Peroxide Sensing, Molecular Cell, 2007, p. 1-14 vol. 26.
Williams, Williams Dictionary of Biomaterials, Liverpool University Press, 1999.
Zhang Li-hua, Radiation Effects and Interphase of Crystalline Polymers, The Sixth Annual Academic Conference of Radiation research and radiation process, Oct. 31, 2004, p. 1-19, (with English machine translation).

* cited by examiner

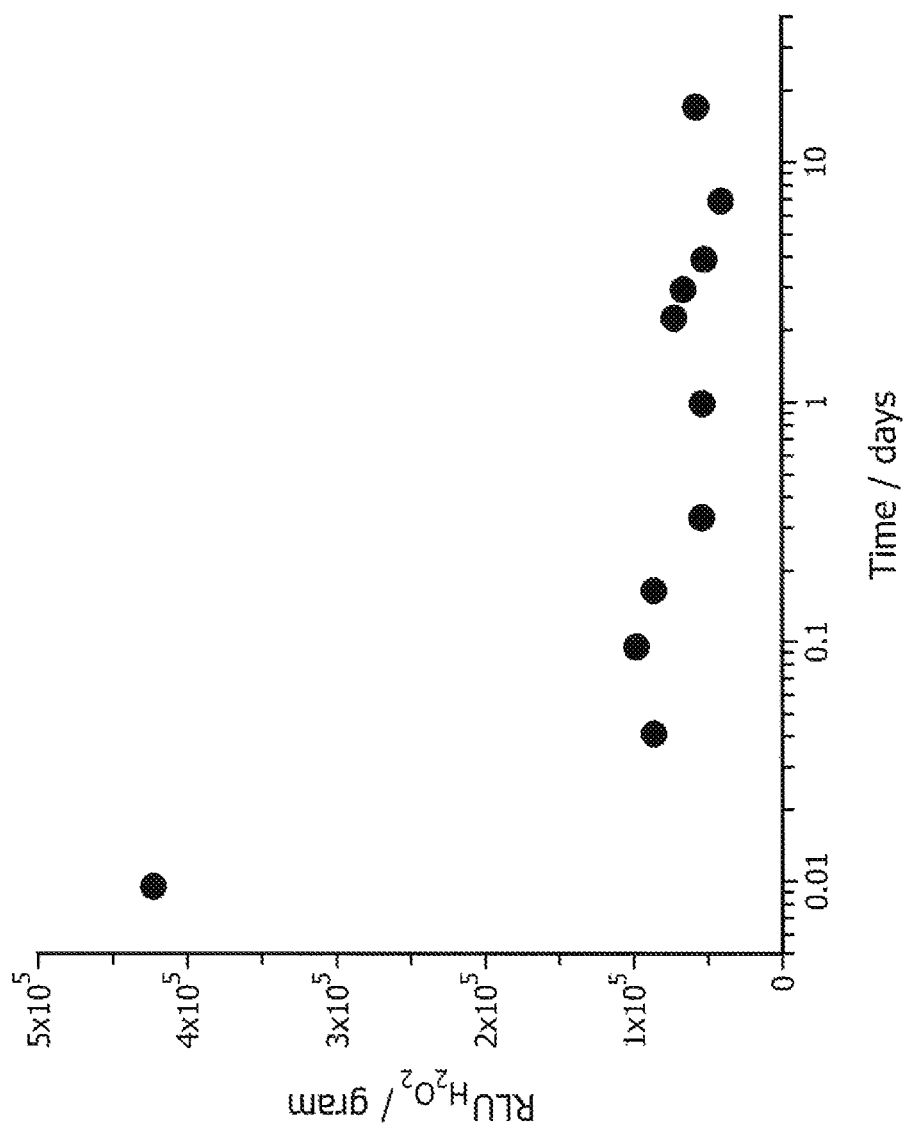

REACTIVE OXIDATIVE SPECIES GENERATING MATERIALS AND METHODS OF USE

FIELD OF THE INVENTION

The present invention relates to materials comprising stabilized free radicals which are capable of generating reactive oxidative species and uses thereof.

BACKGROUND OF THE INVENTION

Sterilization of medical devices may be provided by several means. Two common means are ethylene oxide sterilization (EO) and sterilization by exposure to ionizing radiation. However, exposure of certain polymers and organic materials, common in the production of medical devices, to ionizing radiation has been shown to cause some level of degradation to the polymer or organic material. The extent to which a polymer or organic material degrades is believed to be related to the dose of ionizing radiation absorbed. Thus, where a device is constructed of polymeric or organic materials, the applied radiation dose should be high enough to sterilize the device while concurrently being as low as possible in order to minimize the amount of device degradation that occurs. Where used for permanent and absorbable polymers and copolymers, typical, final packaged device sterilization is achieved with a dose of approximately 25 kGy.

Additionally, certain polymers, when exposed to ionizing radiation, undergo chain scission which may result in the formation of free radical(s) along the affected polymer chain. Free radicals of this type are generally known to exist in polymers for only brief periods of time after generation. The high energy of free radicals makes them unstable, rapidly reacting or recombining whenever possible. If the free radical combines with another free radical, and those free radicals are on differing polymer chains, crosslinking occurs and effectively increases molecular weight. If the free radical formed on the irradiated polymer chain combines with another element such as, but not limited to, oxygen, it may result in a degradation reaction and possibly a decrease in overall polymer molecular weight. In either case, the free radical reaction rate is typically very fast once the necessary conditions exist. Where the free radicals react with an oxygen molecule, reactive oxidative species (ROS) may be generated.

ROS are chemically reactive and biologically active oxygen-containing species such as superoxide, hydrogen peroxide, singlet oxygen, hydroxyl radical, hypochlorite, peroxynitrite, and perhydroxy radical, and combinations thereof. Further, ROS are highly reactive due to the presence of unpaired valence shell electrons.

In biology, ROS serve critical functions involving the immune response. For example, superoxide is naturally generated during "the respiratory burst" by activated neutrophils during phagocytosis of a microbe and is the mechanism used by the engulfing polymorphonuclear leukocytes (PMNs) in order to destroy bacteria. In light of this, current antibacterial drug therapies use ROS, particularly hydroxyl radicals, as the mechanism for bactericidal action (Kohanski et al., Cell, 130, 797-810 (2007)).

ROS are also active in cell signaling, including but not limited to stimulating cell proliferation, differentiation, migration, apoptosis, and angiogenesis (Klebanoff. Annals Internal Medicine, 93, 480-9 (1980)) (Turrens, Jrl Physiol, 552 (2), 335-44 (2003)) (Veal et al., Molecular Cell, 26, 1-14 (2007)). In particular, it has been shown that ROS even at relatively low concentrations (micro- to nanomolar) act as key cell signaling molecules to regulate a variety of biological processes such as angiogenesis, cell proliferation, and cell migration (Veal et al., Mol Cell.; 26(1): 1-14 (2007)) (D'Autrraux et al., *Nature Reviews Molecular Cell Biology*, 8, 813-824 (2007)). ROS have also been shown to be influential in platelet activation (Krotz et al., Arterioscler Throm Vase Biol; 24: 1988-96 (2004)). Involvement in these biological processes places ROS in the critical role of regulating numerous physiologic and pathologic states, including but not limited to some cancers, cardiovascular disease, chronic wounds, aging and neurodegeneration. For instance, use of ROS in clinical therapy has been demonstrated in photodynamic therapy (PDT) for cancer treatment (Dolmans et al., Nature Reviews Cancer, 3, 380-7 (2003)).

Higher level of ROS is known to inhibit cell proliferation and even induce cell apoptosis. Thus, one application of such ROS generation materials is to make medical devices, e.g. stent and balloons, to treat stenosis and restenosis in humoral ducts, including blood vessel, bile duct, esophagus and colon.

A stenosis is an abnormal narrowing in blood vessels or other ducts that is caused by uncontrolled proliferation and deposition of cells, extracellular matrix, lipids and other cellular contents. Thus, materials that release high levels of ROS can be used to inhibit such cellular proliferation and resolve the stenosis through the induction of apoptosis.

Restenosis refers to the recurrence of stenosis that follows the interventions that treat the original stenosis. Restenosis usually pertains to blood vessel that has become narrowed; received treatment to clear the blockage and subsequently become re-narrowed. Restenosis can occur following interventions such as percutaneous transluminal coronary angioplasty and stent treatments. These cardiovascular interventions induce unwanted proliferation of vascular smooth muscle cells (neointimal hyperplasia), which eventually leads to the re-narrowing of blood vessels. To prevent restenosis, drug-eluting stent (DES) was introduced into clinical cardiology at the beginning of the 2000s. Antiproliferative drugs, such as paclitaxel (an anti-cancer drug) and sirolimus (an immuno-suppressive drug), were coated on the surface of cardiovascular stent and released locally to the blood vessel wall. These drugs effectively inhibit vascular smooth muscle cell proliferation, and thus prevent in-stent neointimal hyperplasia and consequently restenosis.

It has been demonstrated that high level of ROS, particularly hydrogen peroxide, can effectively inhibit the proliferation of smooth muscle cells (Deshpande, N. N., et al., *Mechanism of hydrogen peroxide-induced cell cycle arrest in vascular smooth muscle.* Antioxid Redox Signal, 2002. 4(5): p. 845-54) and other cells (Li, M., et al., *Hydrogen peroxide induces G2 cell cycle arrest and inhibits cell proliferation in osteoblasts.* Anat Rec (Hoboken), 2009. 292(8): p. 1107-13) & (Chen, Q. and B. N. Ames, *Senescence-like growth arrest induced by hydrogen peroxide in human diploid fibroblast F65 cells.* Proc Natl Acad Sci USA, 1994. 91(10): p. 4130-4). ROS generating materials thus can be used to make medical devices, such as stent and balloons, which once deployed can locally deliver high level of ROS to prevent/treat restenosis.

To date, the benefits of ROS have been limited due to the short nature of their existence and difficulties in providing them at therapeutic levels and durations to desired treatment sites. It has surprisingly been found that stabilized free radicals can be formed in certain polymers and such free radicals can, in turn, generate ROS when exposed to an oxygen containing aqueous environment. Given the biological relevance of ROS, materials, devices and methods that enable the extended generation of ROS at a treatment site would be advantageous in the medical field and are contemplated herein.

SUMMARY OF THE INVENTION

The present invention relates to materials that comprise stabilized free radicals and the use and manufacture thereof.

More particularly, the present invention includes a biocompatible material comprising at least one semi-crystalline, hydrolytically degradable polymer wherein the polymer has been subjected to ionizing radiation at a total dose from about 30 to about 50 kGy and wherein the biocompatible material comprises stabilized free radicals. In another embodiment, a stabilized free radical containing biocompatible material comprising at least one semi-crystalline, hydrolytically degradable polymer, wherein the polymer has been subjected to ionizing radiation at a dose rate less than about 50 kGy and is sterilized by non-ionizing radiation methods is contemplated. The present invention also relates to a method of providing stabilized free radicals to a treatment site comprising applying the biocompatible, described above.

Another embodiment of the present invention relates to a method of enabling the production of reactive oxidative species from a biocompatible material at a treatment site comprising: applying a biocompatible material comprising a semi-crystalline, hydrolytically degradable polymer comprising stabilized free radicals to a treatment site; exposing said biocompatible material to an oxygen containing aqueous media; and increasing the amount of oxygen relative to atmospheric oxygen accessible to the biocompatible material.

The invention further includes a biocompatible composite that enables multi-phasic production of reactive oxidative species comprising: at least a first hydrolytically degradable, semi-crystalline polymer comprising stabilized free radicals; at least a second hydrolytically degradable, semi-crystalline polymer comprising stabilized free radicals; and wherein said at least first polymer is not the same as said at least second polymer. A biocompatible composite that enables the production of reactive oxidative species when placed in contact with aqueous media comprising at least a first hydrolytically degradable, semi-crystalline polymer which comprises stabilized free radicals and at least a second material wherein the second material modifies the profile of said production of reactive oxidative species is also contemplated herein.

In another embodiment, a biocompatible material is envisioned with an increased capacity to generate reactive oxidative species comprising a hydrolytically degradable, semi-crystalline material wherein the material has been subjected to ionizing radiation while maintained in an inert atmosphere.

The present invention also includes a hydrolytically degradable semi crystalline polymer comprising a concentration of stabilized free radical per crystalline melt enthalpy of greater than 10 units.

Devices incorporating the materials of the present invention are also contemplated herein.

BRIEF DESCRIPTION OF THE DRAWINGS

FIG. 13 is a graphical representation of the hydrogen peroxide content in a sample of irradiated 2:1-PGA/TMC copolymer web measured at various time points upon exposure to an oxygen containing aqueous media.

DETAILED DESCRIPTION OF THE INVENTION

Figure 1:
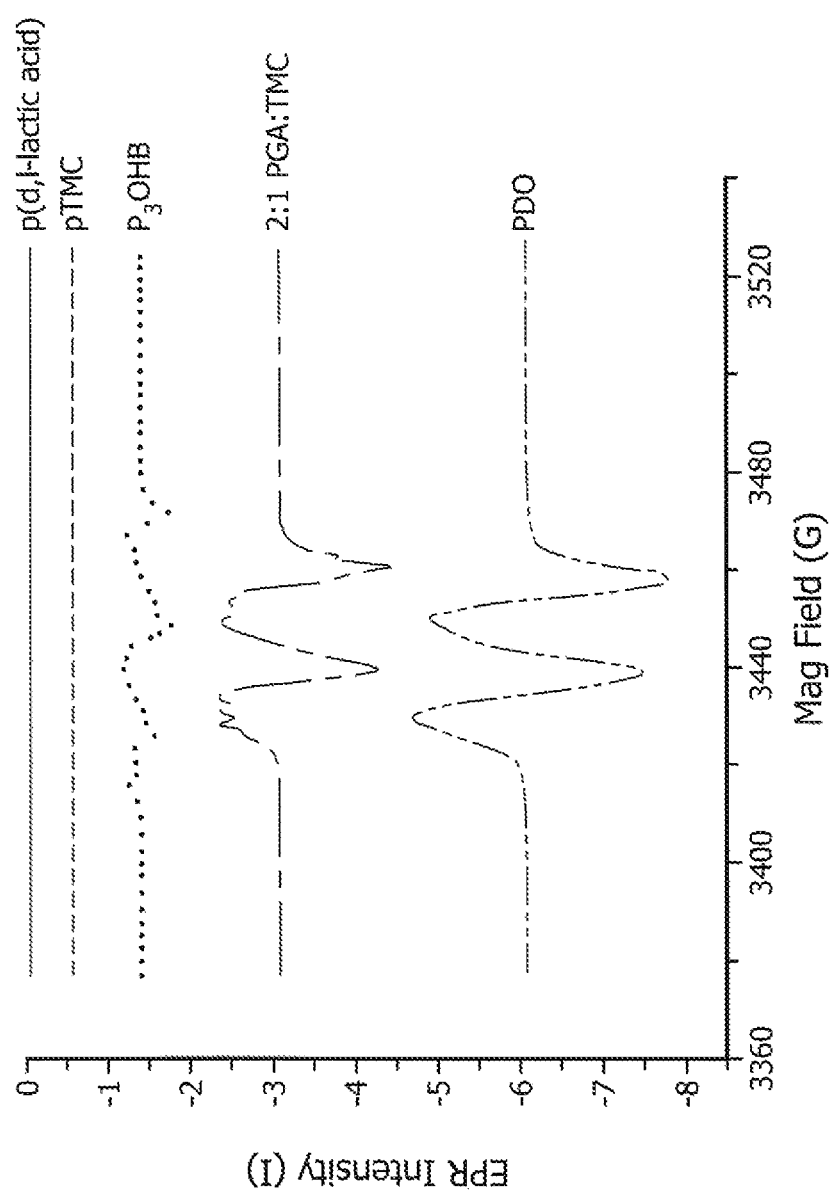
FIG. 1 shows electron paramagnetic resonance (EPR) spectra depicting crystalline and amorphous materials where each spectrum has been offset along the y-axis for differentiation.

The present invention is a semi-crystalline, hydrolytically degradable, biocompatible polymeric material that contains stabilized free radicals after exposure to ionizing radiation. The material is capable of delivering stabilized free radicals to selected target locations such as, but not limited to, a wound or other location on or in the body. Upon contact with an oxygen-containing aqueous media, the free radical containing material can generate reactive oxidative species over an extended period of time.

In one aspect, the present invention relates to a delivery medium comprising a semi-crystalline polymer that has been exposed to a controlled dose of ionizing radiation. For the purposes of this document, the term "polymer" is intended to include both "homopolymers" and "copolymers". Suitable polymers are semi-crystalline due to the presence of amorphous regions and regions of highly ordered molecular structure (crystalline regions). Depending on the chemical structure, polymer crystals may form when a polymer is cooled from the viscous, amorphous state (above the crystalline melting point) to the solid state. In alternate embodiments, polymer crystals can be formed by heating the glassy state polymer to its crystal-perfection temperature, followed by cooling.

In a crystal, the polymer chain itself is able to regularly orient into a tightly packed region. An adjoining amorphous region is more irregularly packed and not as dense. Due to the relatively tight packing of the polymer coil in a crystal, polymer chain movement is restricted in this phase or region of the polymer. The percentage of the polymer that is crystalline is called the "percent crystallinity". The percent crystallinity exerts influence on the properties of the polymer. Percent crystallinity can be determined by analytical techniques such as differential scanning calorimetry (DSC) or spectroscopic methods by relating the test material level of crystallinity to that of an analogous control material at a saturated-crystalline condition. DSC is used to quantify the latent heat of (crystalline) melting and provides an estimate of the energy needed to melt the crystalline fraction.

A polymer or copolymer undergoes hydrolysis when reacting with aqueous media whereby cleavage of the polymer or copolymer chains results. Hydrolysis may proceed to varying extents and rates depending on environmental and other factors. Partial hydrolysis occurs when some but not all of the polymer or copolymer chains have been broken by reactions with water. Being "substantially broken down by hydrolysis" means that a substantial portion of the solid polymer mass is dissolved into the surrounding aqueous fluid resulting in a loss of solid mass of about 20 percent or more, in one embodiment of about 40 percent or more, in another embodiment of about 50 percent or more, in yet another embodiment of about 75 percent or more, and in yet another embodiment of about 95 percent or more. Polymers suitable for use in the present invention are hydrolytically degradable which is defined as the characteristic of a compound (e.g., a polymer or a polymeric adduct) when exposed to aqueous fluids having near neutral pH (e.g., water, blood, perspiration), to be substantially broken down by hydrolysis within 0 to 24 months, in one embodiment within 0 to 12 months, in another embodiment within 0 to 6 months, and in yet another embodiment within 0 to 1 month. The temperature of an aqueous liquid to which a compound is exposed can be between room temperature and about 37 C. In the body, other degradation means such as enzymatic attack may also be present.

One method useful in determining whether a polymer or a polymeric adduct is hydrolytically degradable includes characterizing the behavior of said polymer in a suitable aqueous environment by: (a) depositing the polymer or polymeric adduct on a stable substrate, such as a stent, to make a polymer or polymeric adduct coated substrate; (b) weighing the remaining solid polymer or polymeric adduct coated substrate; (c) immersing the polymer or polymeric adduct coated substrate into an aqueous fluid having near neutral pH; and (d) periodically weighing the substrate. If after exposure for a suitable period of time, a lesser amount of remaining solid polymer or polymeric adduct remains, the polymer or polymeric adduct is considered "hydrolytically degradable".

In medical applications, it is desirable that the polymer be biocompatible meaning a material that has "the ability . . . to perform with an appropriate host response in a specific application" (*The Williams Dictionary of Biomaterials*, D F Williams, Liverpool University Press, 1999). Furthermore, the biocompatible polymer may be bioabsorbable. "Bioabsorbable" means that a substance is substantially broken down by the in vivo environment in an amount of time of 1 to 24 months; in one embodiment, in an amount of time of from 1 to 18 months; in another embodiment, in an amount of time of from 1 to 12 months. Biocompatible, semi-crystalline, hydrolytically degradable polymers suitable for use in the present invention include, but are not limited to, poly(dioxanone) (PDO), poly(glycolide) (PGA), poly(lactide) (PLA), poly(ε-caprolactone), poly(anhydrides) such as poly(sebacic acid), poly(hydroxyalkanoates) such as poly (3-hydroxybutyrate) (P3OHB), and any other polymers meeting the definition of biocompatible, semi-crystalline, and hydrolytically degradable. Biocompatible, semi-crystalline, hydrolytically degradable copolymers suitable for use in the present discovery include, but are not limited to, copolymers of the above polymers such as poly(glycolide)/trimethylene carbonate (PGA/TMC), poly(lactide)/trimethylene carbonate (PLA/TMC), poly(hydroxybutyrate/hydroxyvalerate (PHB/PHV), and any other copolymer that is biocompatible, semi-crystalline, and hydrolytically-degradable. Copolymers referenced herein are described based on a weight ratio of the first polymer to the second polymer (e.g. 2:1-PGA/TMC means two parts of PGA to one part of TMC based on weight).

Ionizing radiation is radiation composed of particles or photons that individually can liberate an electron from an atom or molecule, producing ions, which are atoms or molecules with a net electric charge. Types of ionizing radiation that can affect a polymer chain include, but are not limited to, X-rays, electron beam (e-beam), and gamma radiation. Amongst the differing types of ionizing radiation, the energy and depth of penetration into an article varies. For example, gamma radiation, which are (electromagnetic) photons emitted from a radioactive source, typically have energies in the 0.7 (Cesium-137) up to 1.3 (Cobalt-60) Megaelectronvolts (MeV) range. Given the form and energy, gamma radiation is highly penetrating, even into dense articles, and as such has found use as a mode of bulk irradiation (extending into entire bulk shipment), generally for sterilization. E-beam irradiation on the other hand, are accelerated electrons (particles) emitted from an electron gun, and thus can be adjusted to a wide range of energies from 1 eV up to >1 MeV. Given the form and energy range, e-beam irradiation is not nearly as penetrating as gamma radiation, and the depth of penetration is furthermore affected by the irradiated article density. As such, e-beam has found application in entire device sterilization, and in material modification where it is desired to partially irradiate into a material, for property modification or subsequent chemical reaction(s), yet leave the underlying material, structure, or substrate unaffected.

The absorbed dose, or amount of irradiation subjected to an article is typically reported in units of "grays" or "rads", where 1 rad=0.01 gray (Gy). Even more typically, absorbed dose is reported in "kilograys" or "megarads", where 1 kGy=0.1 Mrad. In medical applications, irradiation of materials has been shown to be useful for the purpose of sterilization. Where used for permanent and absorbable polymers and copolymers, typical, final packaged device sterilization is achieved with a dose of approximately 25 kGy.

However, certain polymers, when exposed to ionizing radiation, undergo chain scission which may result in the formation of free radicals along the affected polymer chain. As used herein, the term "free radicals" is defined as atoms, molecules, or ions with unpaired electrons or an open shell configuration. Free radicals may have positive, negative, or zero charge. With few exceptions, these unpaired electrons cause radicals to be highly chemically reactive. The materials of the present invention are achieved by exposing biocompatible, semi-crystalline, hydrolytically-degradable polymers to ionizing radiation via any means known in the art in order to generate stabilized free radicals therein. Any type of ionizing irradiation may be used, such as gamma and e-beam. Whole article (bulk) irradiation is easily realized with gamma irradiation, and with e-beam irradiation (at sufficiently high eV energy). Partial article irradiation can be achieved with a lower energy e-beam treatment. Any amount of ionizing radiation may be used, in one embodiment the dose is less than about 50 kGy, and in another embodiment the dose is from about 30 kGy to about 50 kGy. In another embodiment, low levels of ionizing radiation may be applied with sterilization being achieved by alternative methods. In yet another embodiment, the biocompatible semi-crystalline, hydrolytically-degradable polymers have been subjected to ionizing radiation at a dose that exceeds that required for sterilization but is less than that required to substantially degrade the polymer.

The materials are then useful for controllably delivering these stabilized free radicals to a target location over a controllable period of time. As used herein, what is meant by "stabilized free radicals" are radicals that are formed in a protective matrix, such as a crystal or crystalline structure, and therefore are unable to react or be consumed in a chemical reaction until such matrix is sufficiently degraded to allow exposure of the radical to the surrounding environment. The concentration of stabilized free radicals can also be affected through varying process parameters such as, but not limited to, level, duration, and energy level of ionizing radiation exposure, degree of crystallinity within the semi-crystalline polymer, presence of additives such as scavengers, and order of process steps.

A suitable tool to detect for and analyze free radicals in a given material is electron paramagnetic resonance (EPR). This method is synonymous to what's reported in the literature as ESR, or electron spin resonance. In the simplest of terms, the mere presence of an EPR "signal" or "spectrum" confirms the presence of free radicals in a given material interacting with the magnetic field applied by the EPR. In the absence of free radicals, one would observe no EPR spectra and would see only a flat line. The EPR measurements shown in FIG. 1 show the existence of free radicals in the semi-crystalline polymeric embodiments of the present invention (PDO, 2:1-PGA/TMC, and P3OHB). In contrast, the amorphous polymers in FIG. 1 (d,l-lactide and pTMC) show little or no EPR signal, indicating the absence of free radicals.

Figure 2:
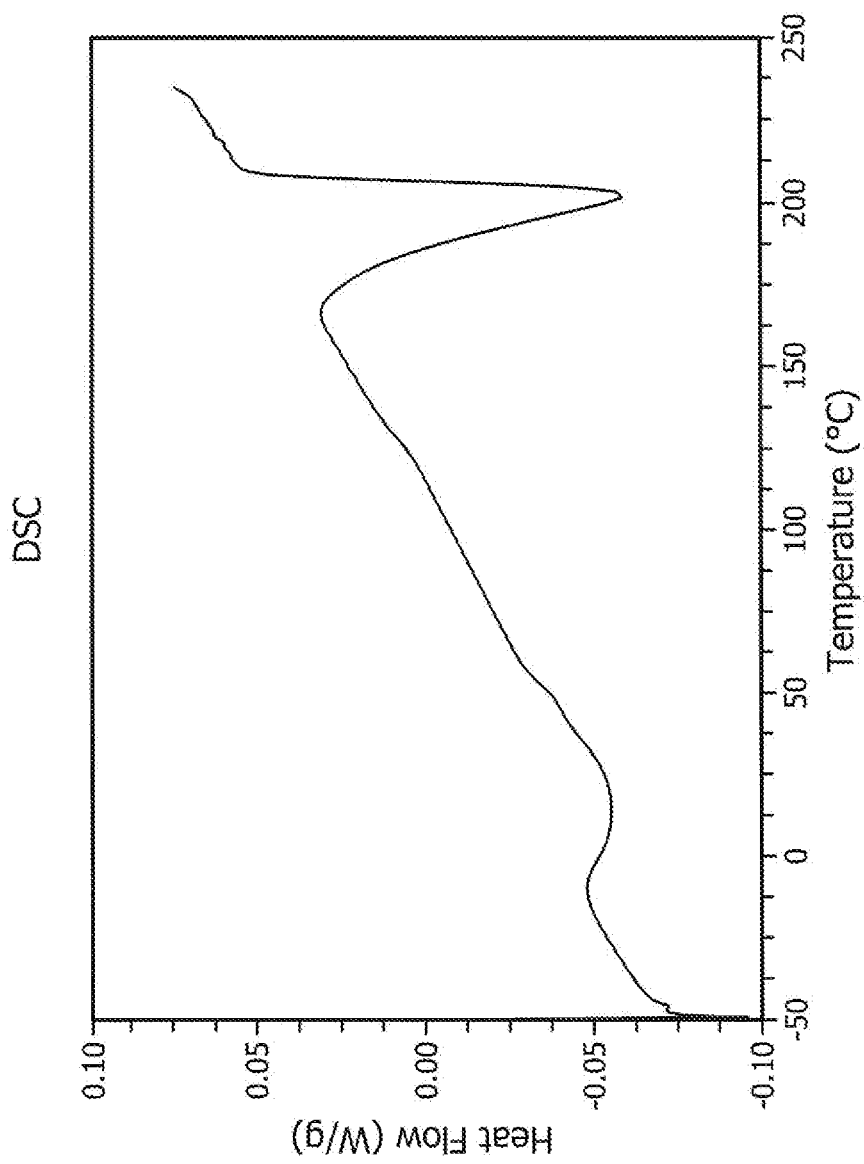
FIG. 2 is a differential scanning calorimetry (DSC) curve of a representative semi-crystalline hydrolytically degradable polymer.
Figure 3:
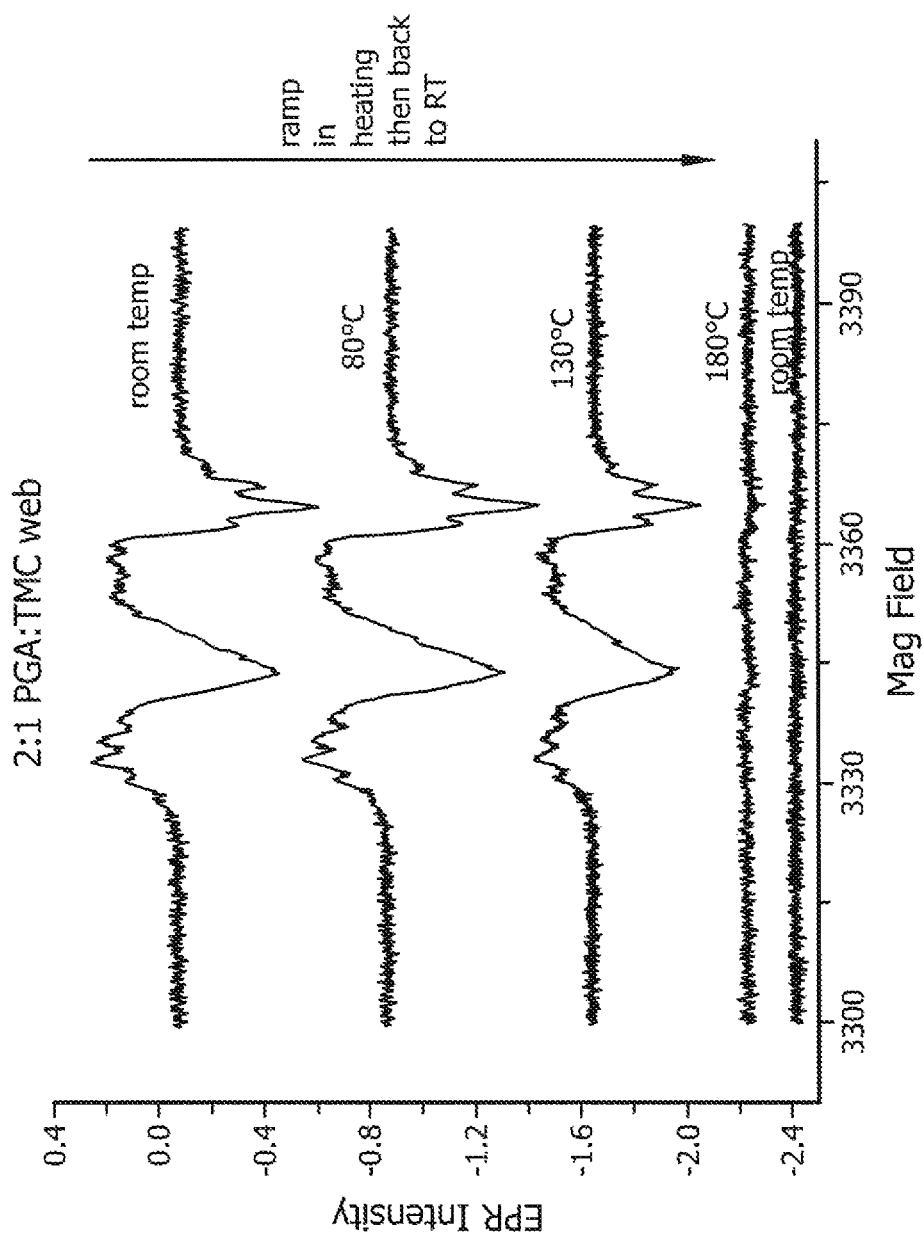
FIG. 3 shows EPR spectra indicating free radical content of a representative semi-crystalline, hydrolytically degradable polymer across a given temperature range.

Furthermore, the semi-crystalline, hydrolytically degradable polymeric embodiments of the present invention show the disappearance of the free radical peaks as the temperature of the semi-crystalline polymer approaches the melt temperature of the crystalline domains. For example, the crystalline melt temperature of the 2:1-PGA/TMC copolymer is approximately 200° C., with a significant melt endotherm observed from 180 to 200° C., as shown in FIG. 2. During melting, the polymer chain mobility increases significantly, increasing the probability of free radical recombination and reaction with other substances. As shown in FIG. 3, the EPR signal of 45 kGy gamma irradiated, 2:1-PGA/TMC is present at room temperature, 80° C. and 130° C. At 180° C., the crystalline domains begin to melt and the EPR signal decreases. Cooling from 180° C. back to room temperature does not regenerate free radicals as evidenced by no EPR peaks. Once the free radicals are liberated by the crystalline domains of the semi-crystalline polymer melting, they do not spontaneously reform.

Figure 4:
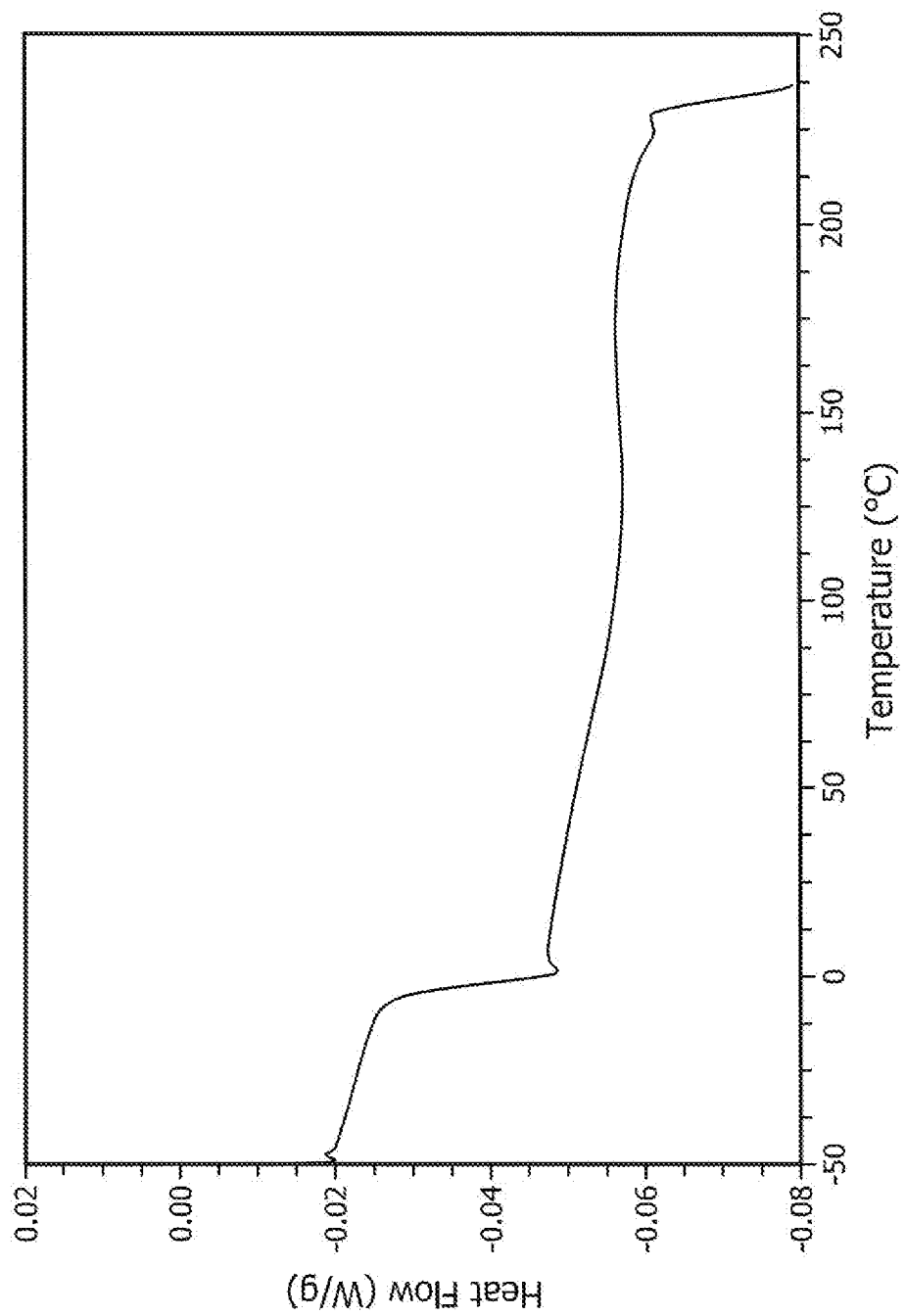
FIG. 4 is a DSC curve of an amorphous polymer.
Figure 5:
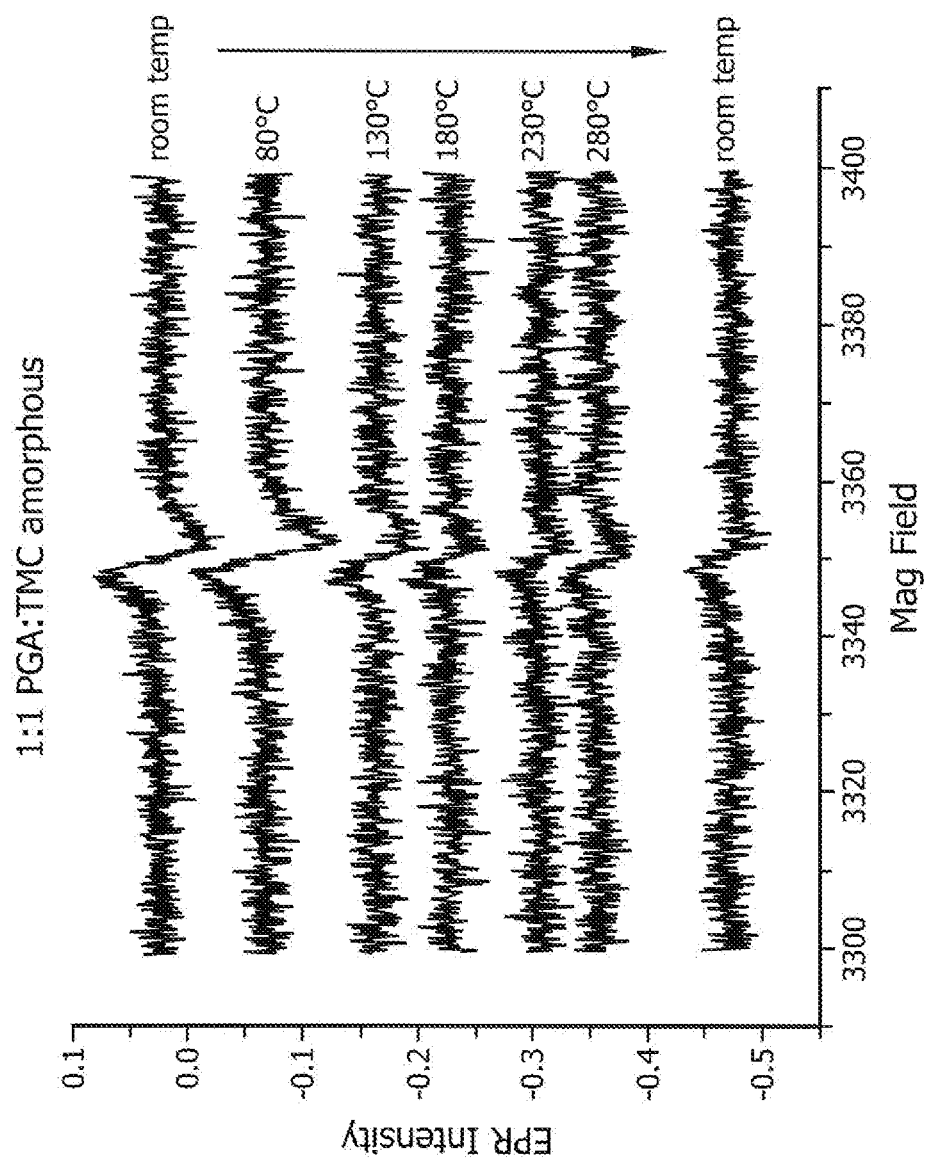
FIG. 5 shows EPR spectra indicating the free radical content of an amorphous polymer across a given temperature range.

FIG. 4 is a DSC curve of the same comonomers of the above example [glycolide (GA) and trimethylene carbonate (TMC)] is 1:1-PGA/TMC having a random chain structure and little or no crystalline domain. After gamma irradiation at 45 kGy, this non-crystalline, amorphous copolymer form does not exhibit a significant EPR signal. As shown in FIG. 5, the signal is less than 0.1 (units). It is important to note the change in the scale reflected in FIG. 5 versus that of FIG. 4. Upon heating, the trace EPR signal is unaltered up to 280° C. Subsequent cooling back down to room temperature does not create a significant EPR signal. Absence of an EPR signal confirms that this amorphous, irradiated, random copolymer contains virtually no stabilized free radicals.

Figure 6:
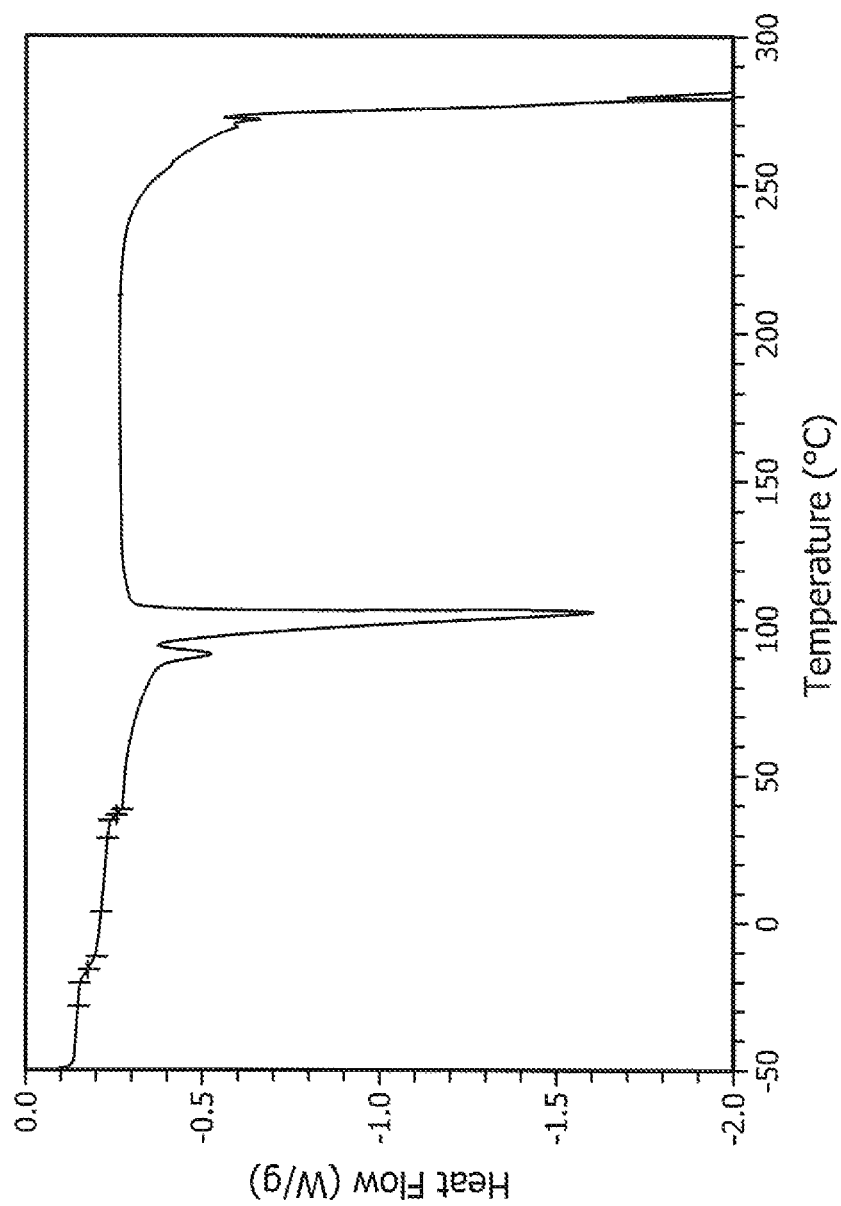
FIG. 6 is a DSC curve of a representative semi-crystalline hydrolytically degradable polymer, specifically polydioxanone.
Figure 7:
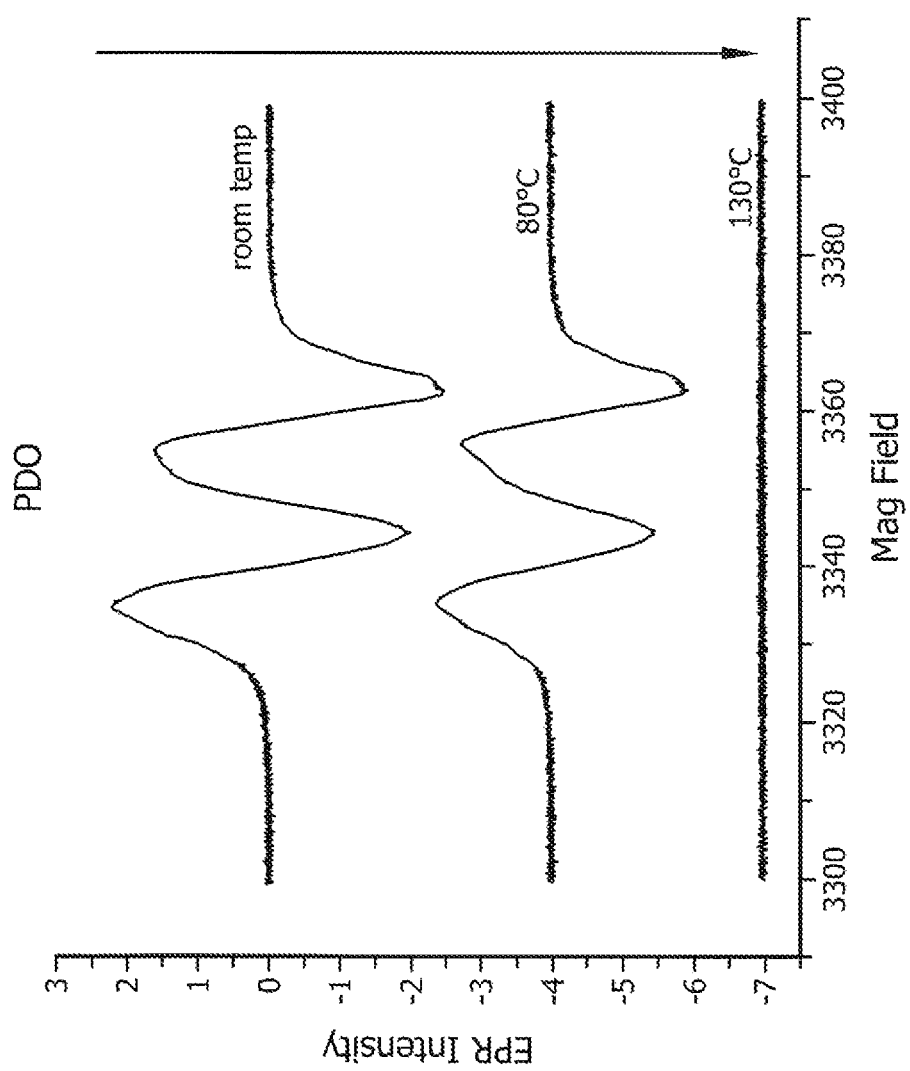
FIG. 7 shows EPR spectra indicating the free radical content of a representative semi-crystalline, hydrolytically degradable polymer, specifically polydioxanone, across a given temperature range.

Another example of this phenomenon can be seen in FIG. 6 which incorporates use of polydioxanone (PDO) which has a crystalline melt temperature of approximately 110° C. As shown in FIG. 7, after gamma irradiation at 45 kGy, the PDO semi-crystalline hydrolytically degradable polymer exhibits a strong EPR signal at room temperature and upon heating to 80° C. However, once the crystalline melt temperature is reached, the EPR signal disappears and no free radicals remain (FIG. 7).

Figure 8:
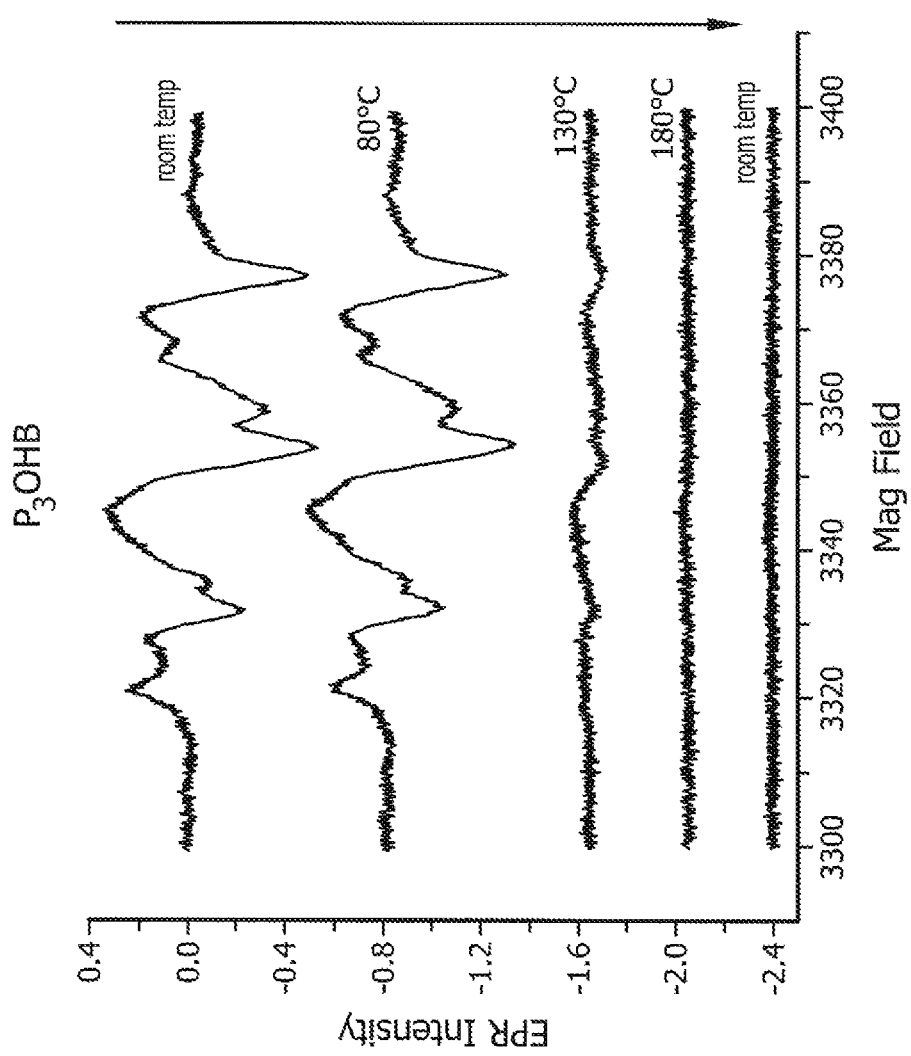
FIG. 8 shows EPR spectra indicating the free radical content of a representative semi-crystalline, hydrolytically degradable polymer, specifically poly(3-hydroxybutyrate), across a given temperature range.
Figure 9:
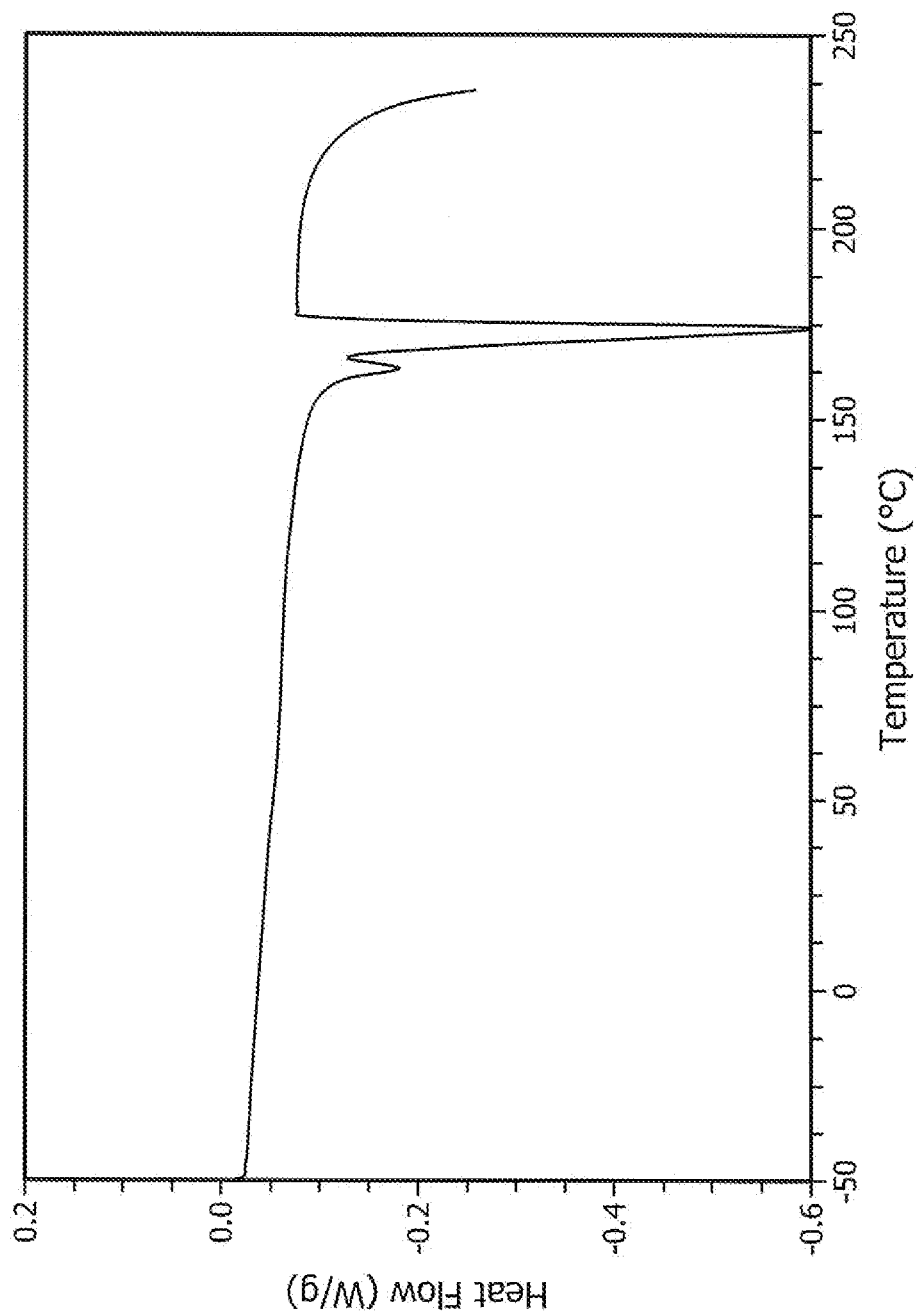
FIG. 9 is a DSC curve of a representative semi-crystalline hydrolytically degradable polymer, specifically P3OHB.

EPR measurements also show the existence of free radicals in another bioabsorbable hydrolytically degradable semi-crystalline polymeric embodiment of the present invention, poly-3-hydroxybutyrate (P3OHB). P3OHB has a crystalline melt temperature of approximately 170° C. (FIG. 9). As shown in FIG. 8, the EPR signal of 45 kGy gamma irradiated, P3OHB is strong at room temperature and upon heating to 80° C. and 130° C., but then disappears as the temperature is further increased above the crystalline melt to 180° C. Cooling from 180° C. back to room temperature does not recreate an EPR signal. Again, once the free radicals are liberated by melting the crystalline domains of the semi-crystalline polymer, new free radicals do not spontaneously reform.

Figure 10:
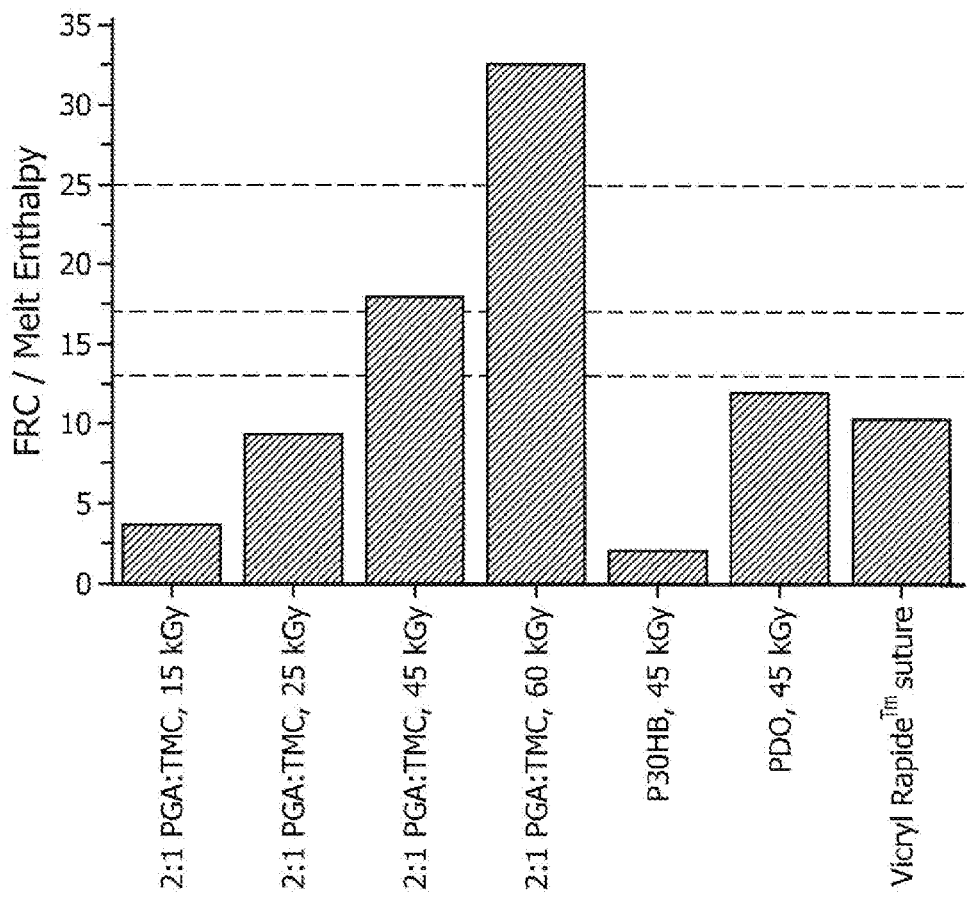
FIG. 10 is a graphical representation of the free radical content per melt enthalpy for a several materials subjected to varied conditions.

The movement of polymer chains is restricted within the crystalline phase of a polymer. For a given dose of ionizing energy, the stability of the free radicals generated by the irradiation is related to the degree of movement restriction within the crystalline phase. DSC assesses the latent heat of melting to provide an estimate of the energy required to melt the crystalline fraction (i.e. to overcome the restrictive forces of a crystal). The energy required to melt the crystalline fraction is determined by integrating the area of the melt endotherm on a DSC trace and is referred to as the melt enthalpy. As described above, EPR is used to detect free radicals and can provide an estimate of the free radical concentration in a given material. This estimate of the free radical concentration is determined by double integration of the EPR spectra per unit weight of sample (reference book "Quantitative EPR" by Eaton et al., p. 30, 2010). The combination of the two, in which the double-integrated EPR intensity per unit weight of sample is divided by the melt enthalpy, can provide an overall estimate of free radical concentration per unit crystallinity. Material embodiments with a more tenacious crystalline phase are more likely to provide safe harbor for a formed free radical. This more effective storage of stabilized free radicals in semi-crystalline, hydrolytically degradable polymers is useful in providing higher concentration of free radicals per crystal. FIG. 10 indicates high concentrations of free radicals per crystalline melt enthalpy, greater than 10 units, for samples of the semi-crystalline, hydrolytically degradable, bioabsorbable 2:1-PGA/TMC after exposure to 45 kGy of gamma irradiation and after 60 kGy of gamma irradiation. The resulting effect demonstrates that high concentrations of stabilized free radicals that can persist in biocompatible, semi-crystalline, hydrolytically degradable polymers exposed to increased levels of ionizing radiation. In one embodiment the concentration of free radicals per crystalline melt enthalpy is greater than 10 units. In another embodiment the concentration of free radicals per crystalline melt enthalpy is greater than 15 units. In yet another embodiment, the concentration of free radicals per crystalline melt enthalpy is greater than 20 units.

Stabilized free radicals secured within the biocompatible, semi-crystalline, hydrolytically degradable, polymer can be controllably accessed upon exposure to an aqueous medium where polymer hydrolysis ensues. The pH and/or temperature of the aqueous medium may also affect rate of hydrolysis and hence the rate of access to the stabilized free radicals. Suitable aqueous media include but are not limited to water, aqueous buffer solution, biological fluids, and water vapor. Once accessed in an aqueous medium, the free radicals are available to react with dissolved oxygen in the aqueous media. "Oxygen containing aqueous media" means any fluid comprising water, or otherwise being capable of hydrolytic degradation of materials, and oxygen. In biological systems, suitable oxygen-containing aqueous media include, but are not limited to, wound exudate, blood, serum, perspiration, and extracellular fluid. For instance, an aqueous media would be present within the body, within a wound bed, at the skin surface, at any mucosal surface, as well as other areas.

Where the free radicals react with an oxygen molecule, reactive oxidative species (ROS) may be generated. For instance, when reacting with dissolved oxygen, free radicals reduce molecular oxygen to generate superoxide, $O_2.-$. Superoxide is part of a broad family of active compounds dubbed reactive oxygen species, or ROS. Superoxide can spontaneously or catalytically break down to hydrogen peroxide ($H_2O_2$). It has been reported that superoxide can also react with nitric oxide (NO.) to form peroxynitrite (ONOO—). Aqueous fenton reactions of hydrogen peroxide also lead to hydroxyl (.OH) and perhydroxy radicals (.OOH). The above and other compounds such as singlet oxygen ($^1O_2$), hypochlorite (ClO—), and all combinations thereof, are included in the ROS family.

Due to the stability of free radicals in the crystalline portions of the materials of the present invention, ROS can be generated over an extended period of time. By "extended period of time" is meant persisting for more than a minimum of 24 hours, in one embodiment for more than a week, in another embodiment for more than a month.

Superoxide's evanescent nature requires select methods of detection. One suitable method to detect superoxide involves the use of a chemiluminescent compounds such as luminol, or yet another being the photoprotein Pholasin® (Knight Scientific Ltd., Plymouth, UK), with a suitable spectrophotometer such as the FLUOstar Omega microplate reader (BMG Labtech Inc., Cary N.C.). Pholasin® will react with superoxide and other ROS to yield light, or illuminate. Attribution to superoxide specifically is determined by the Pholasin® chemiluminescent signal difference between sister sample wells, one of which includes superoxide dismutase (SOD), an enzyme that catalyzes the superoxide dismutation reaction in which superoxide is converted into oxygen and hydrogen peroxide. Irradiated embodiments herein demonstrate the formation and presence of stabilized free radicals, and the generation of superoxide ($O_2.-$) once exposed to oxygen-containing aqueous media. Furthermore, irradiated 2:1-PGA/TMC copolymer embodiments herein demonstrate a non-linear trend between irradiated dose and ROS (including superoxide) generation, in particular between the levels of 30 to 50 kGy (FIG. 10).

Another ROS species that are capable of being generated by materials and methods of the present invention is singlet oxygen. With a suitable spectrophotometer, MCLA (2-methyl-6-(p-methoxyphenyl)-3,7-(dihydroimidazo[1, 2alpha]pyrazine-3-one)) can be used to detect singlet oxygen. In this instance, attribution to singlet oxygen is determined between sister samples, one of which includes sodium azide ($NaN_3$), which quenches singlet oxygen (Bancirova, Luminescence, 26 (6), 685-88 (2011)). Irradiated embodiments herein demonstrate the formation and presence of stabilized free radicals, and the generation of singlet oxygen once exposed to oxygen-containing aqueous media.

Hydrogen peroxide is yet another ROS species capable of being generated by the materials and methods of the present invention. Amplex® Red (Molecular Probes, Eugene, Oreg.) may be used as a fluorescent probe for hydrogen peroxide using a microplate reader. Attribution to hydrogen peroxide is quantified by the luminescent reduction observed in a sister sample that contains the enzyme catalase, which decomposes hydrogen peroxide to water and oxygen. Irradiated embodiments herein demonstrate the formation and presence of stabilized free radicals, and the generation of hydrogen peroxide once exposed to oxygen-containing aqueous media.

In addition to oxygen present in the aqueous media, in some embodiments, the materials of the present invention may further comprise an oxygen generator. As used herein, the term "oxygen generator" is defined as any component capable of generating oxygen. When incorporated in the materials of the present invention, the oxygen generator is advantageous as the additional oxygen becomes available to react with the stabilized free radicals of the material to potentially drive further generation of reactive oxidative species. Ability to modify ROS generation through varying oxygen availability may be desired given the range of biological processes which are affected by ROS at different concentrations and/or durations.

In light of the chemically reactive nature of ROS, it may be advantageous to incorporate additional compounds into the materials of the present invention which are capable of reacting with ROS. For example, a nitrogen containing compound is capable of reaction with ROS to product nitric oxide and may be incorporated in the materials or devices described herein. Similar to ROS, nitric oxide is a mediator of multiple biological processes and is known to play critical roles in physiologic and pathologic states, including but not limited to, cardiovascular health and disease.

Given the ability of stabilized free radicals to react in a controllable manner and generate biologically active molecules, such as ROS, methods for providing them to desired treatment sites are the foundation for therapeutic use. For example, a superoxide generating material as described herein can be placed on or near a treatment site, such as but not limited to a wound, so that the superoxide produced can aid in the healing process. The contact between the treatment site and the material comprising stabilized free radicals may be direct or indirect. For instance, a layer of therapeutic compositions or other medical materials may be located between the treatment site and the present materials. The stabilized free radical containing material may then remain in close proximity to the treatment site for a desired period of time.

In addition, following application of the inventive material at the desired treatment site, varied mechanisms for enhancing production of ROS at the treatment site may be utilized. For instance, further enhancing ROS production by applying a material comprising stabilized free radicals, exposing the material to an oxygen-containing aqueous environment and modulating the amount of oxygen accessible to the material. Accessible oxygen may be increased by increasing the atmospheric oxygen concentration by hyperbaric oxygen therapy, for example. In another example, the local atmospheric oxygen concentration may be modulated by topical oxygen therapy. The quantity of oxygen delivered by the blood may be increased by increasing the concentration of oxygen in the blood. For example, oxygen content of the blood could be increased by increasing the number of red blood cells available. Additionally, release of oxygen by red blood cells could be increased by a reduction in pH via the Bohr Effect. To increase the overall quantity of blood supplying oxygen, perfusion can be increased at the treatment site. Methods for increasing perfusion include applying negative pressure wound therapy, surgical or interventional treatment. In addition, as described above, an oxygen generating component can be incorporated into the biocompatible, semi-crystalline, hydrolytically degradable material therefore increasing oxygen available for reaction with the stabilized free radicals.

Depending on desired use, the present materials comprising stabilized free radicals may take multiple forms such as any some two-dimensional or three-dimensional configuration including but not limited to a wound dressing, a burn dressing, a salve, a suspension, a skin substitute, a tissue scaffold, a sheet, a paste, a fiber, an emulsion, gels, micelles, coatings, solutions, or powder, or combinations thereof. Different forms of the material comprising stabilized free radicals may have different specific surface areas which in turn may impact the generation of ROS. In some instances, the biocompatible polymeric material may have a specific surface area from about 0.001 $m^2$/gm to about 50 $m^2$/gm. By "specific surface area" is meant the sum of the accessible surfaces of all the particles, fibers, foams, and/or porous structures present in unit volume or mass. This specific surface area depends upon the shape, size, porosity, and microstructure of the material. It can be measured by gas adsorption method. The specific surface area is calculated from the BET equation based on the specific retention volumes which are determined from the gas chromatograms of heat desorption. Nitrogen is typically used as an adsorbate.

One potential form is a sheet which is defined as either a flexible or rigid layer wherein the ratio of either its breath or width to its thickness is greater than 10:1. For the purposes of this application, a sheet may consist of a relatively planar arrangement of deposited filaments. By "filament" is meant a fiber or fibers of substantial length. A sheet made by laying down or assembling fibers is known as a web. Webs and other materials may be non-woven, meaning they are made from long fibers, bonded together by chemical, mechanical, heat or solvent treatment. Furthermore, a fiber is defined as a cylindrical or tubular structure wherein the ratio of the length to diameter is generally greater than 100:1 and the diameter is generally less than about 5 mm. Suitable ROS generating sheet materials may have a thickness between 1 µm and 20 mm. Some preferred embodiments have a thickness between 100 µm and 10 mm. The sheet thickness and density can be tailored to provide greater conformability to the desired surface topography, such as conforming to the treatment site.

A pliable form of the inventive material may be chosen so that it may be effectively applied to the target location where the generation of ROS is desired. When used in an emulsion, slurry, or suspension form, the ROS generating material may be provided to the body by a syringe or other suitable fluid delivery device. When used in a paste, gel, or ointment form, the ROS generating material may be provided to the treatment site by a spatula or other suitable viscous fluid delivery device. When used in a powder or particle form, the ROS generating material may be sprinkled or sprayed or deposited on the desired treatment site by any suitable means. Because the different forms of the ROS generating material may have different specific surface areas and/or aspect ratios, the form chosen is one method of affecting the concentration and duration of ROS that is produced at the treatment site.

While the material does not need to be porous, in certain cases porosity or an increased surface area may be desired so that the oxygen-containing aqueous media can infiltrate the open spaces of the material. By "porous" is meant a material has a bulk density less than that of the intrinsic density of the material itself. Porosities in the range of 5 percent up to 99 percent are typically sufficient to enhance biological fluid contact and affect ROS generation at the site. It may be useful to have a porosity in the range of 10 percent up to 90 percent in some circumstances. An additional advantage of the porous ROS generating materials described herein is their ability to function as a tissue scaffold. As a tissue scaffold, the porous ROS generating material may induce neo-vascularization, fill with collagenous tissue, serve as a cell growth medium, stimulate cell migration into the material and promote cell proliferation and differentiation, and/or absorb over time. Changing porosity can alter ROS generation characteristics as needed to affect biological processes and therefore may be tuned depending on the desired application.

Another useful characteristic of the ROS generating materials herein is that it can be provided in a three-dimensional shape or can be shapeable. By "shapeable" is meant the ability of a structure to conform or adapt to a particular contour, form, pattern, or fit. Three dimensional shapes or shapeable materials may be desirable in order to fill void spaces or contact irregular topography at or around a treatment site or treatment location. Envisioned embodiments include, but are not limited to, a plug, tube, stent, fuzz, coil, foam, sling, clip, particle, chip, and variations thereof.

Yet another advantage of the present ROS generating material is that it can be formed from a pigmented or dyed material, or naturally colored material to enhance visualization. For example, a yellow ROS generating material can be used for easy visualization of granulation tissue, which is characterized by a bright red, cobblestone appearance.

In addition to the range of forms which the inventive material may take, composites of multiple materials are envisioned. As used herein, composites are materials made from two or more constituent materials with significantly different, properties that, when combined, produce a material with characteristics different from the individual components. Specifically, composites which enable the multiphasic generation of ROS would be valuable for impacting the numerous biologic processes influenced by the presence of ROS. For instance, these composites could comprise two or more different hydrolytically degradable, semi-crystalline polymers each comprising stabilized free radicals but which very in terms of their ROS generation profiles. Upon exposure to aqueous media, these composite materials can exhibit multi-phasic generation of reactive oxidative species. Multi-phasic generation of ROS may be achieved where the component polymers of the composite contain a different amount of stabilized free radicals. In one embodiment, the generation of ROS may be altered by modifying the hydrolytic degradation rate of at least one of the component polymers, thus altering access to the stabilized free radicals. In another embodiment, the generation of ROS may be altered by modifying the degree of crystallinity of at least one of the component polymers, thus altering the ability of the polymer to stabilize free radicals. In yet another embodiment, the generation of ROS may be altered by modifying the radiation dose of at least one of the component polymers, thus altering the number of free radicals formed during chain scission. In yet one more embodiment, the generation of ROS may be altered by modifying the radiation dose and depth of penetration in a polymer or a polymer composite. For certain applications, it is envisioned that at least one of the component polymers may be bioabsorbable.

Alternatively, a composite material may be envisioned that could provide an initial burst of ROS and a sustained period of ROS generation. In one embodiment, a composite blend of two different hydrolytically degradable, semi-crystalline polymers may be used to provide an enhanced burst of ROS where upon exposure to oxygen-containing aqueous media, the quantity of reactive oxidative species produced by the blend is greater than the weighted average of reactive oxidative species produced by the at least two individual hydrolytically degradable semi-crystalline polymeric materials having been subjected to ionizing radiation at the given radiation dose.

In addition to composites wherein the component polymers contain stabilized free radicals, composites comprising at least one stabilized free radical containing material and at least a second material wherein the second material does not contain stabilized free radicals are envisioned and would be valuable by providing a strengthened, stable, partially permanent device that is capable of generating ROS. Such a composite comprising at least one stabilized free radical containing material and at least a second material wherein the second material does not contain stabilized free radicals may be achieved via the coating of the first material onto the second material substrate. The coating can be done by dissolving the desired first material into solution and applying it on a substrate second material, such as expanded PTFE, and removing the solvent. Furthermore, a coating can also be performed by the sputter deposition of small particles of the first material onto the second material substrate and subsequent bonding or fusion. Such a coating can vary in surface coverage on the substrate as well as thickness and porosity. Such a coated article can be thereafter subjected to partial-depth irradiation to generate the stabilized free radicals only in the hydrolytically degradable, semi-crystalline polymer layer.

A composite comprising at least one stabilized free radical containing material and at least a second material wherein the second material modifies the profile of ROS generation are envisioned. The modifying material may achieve its effect by altering the quantity, rate or duration of ROS or combinations thereof. One mechanism for altering the profile of ROS is for the second material to alter accessibility to the stabilized free radicals. In an additional approach to alter ROS generation, the modifying material may contain an oxygen generator and/or a desiccant. In another embodiment, the modifying material may contain a scavenging component where potential targets of scavenging may include oxygen, singlet oxygen, hydrogen peroxide, superoxide and combinations thereof. Furthermore, the modifying material may contain an enzyme such as superoxide dismutase, which reacts with superoxide, or a catalase, which reacts with hydrogen peroxide. The inclusion of an oxygen generator, desiccant, scavenging component and/or enzyme in the second material would alter the profile of ROS generated and could be tuned for specific applications. Additionally, the modifying material may participate in a chemical reaction with ROS thus altering its profile. Furthermore, the modifying material may be capable of generating an exothermic or endothermic reaction upon contact with aqueous media. Addition or removal of thermal energy may modify movement of polymer chains and/or kinetics of other chemical reactions thus changing the profile of ROS generation.

Composites comprising at least one stabilized free radical containing material and a therapeutic bioactive agent(s) are envisioned. Bioactive agents in this context can be selected from the group consisting of osteoconductive substances, osteoinductive substances, growth factors, chemotactic factors, morphogens, pharmaceuticals, proteins, peptides, and biologically active molecules of autogenic, allogenic, xenogenic or recombinant origin such as transforming growth factor beta (TGF-beta), bone morphogenici proteins (BMPs), antibiotics, antimicrobials, vascular endothelial growth factor (VEGF), basic fibroblast growth factor (bFGF), platelet derived growth factor (PDGF), insulin like growth factor (IGF), insulin, immunoglobulin type G antibodies and combinations thereof.

Given the biological relevance of ROS, the use of a ROS-generating article in combination with other therapeutic compounds, such as an antibiotic or anticancer drug, is also envisioned. A ROS generating implant device could be used in combination with any class of systemically administered antibiotic compounds, such as quinolones, beta-lactams, and aminoglycosides, and may result in a more efficacious treatment by permitting a permanent implant to be placed in a contaminated or infected field. Such a combination may also be efficacious with a lower administration of antibiotic, diminishing the resistance or extending the longevity of such compounds. Furthermore, a ROS generating device could be used in combination with other antimicrobial agents including, but not limited to, silver, chlorhexidine and combinations thereof. The resultant combination therapy may provide an implant that is resistant to bacterial colonization, again, enabling placement in a highly contaminated or infected field. A ROS generating device used in combination with an anticancer drug, like the topoisomerase II inhibitors such as Paclitaxel™, may enable a more efficacious treatment where the device provides a local delivery of ROS and enables a lower systemic dose of the chemotherapeutic drug to be administered.

The modifying material may also act as a barrier to elements including, but not limited to, moisture and/or oxygen, which would affect the reduction of oxygen to ROS by the free radicals. In another embodiment, the modifying material may function as a diffusion barrier. Diffusion restrictions could include reactive components or reaction products thus altering the ROS generation profile. One or more of the component materials in the composite of a stabilized free radical containing material and a modifying material may contain additional compounds such as an oxygen generator and/or a nitrogen containing compound which could react with ROS to product nitric oxide.

Composites as described herein are anticipated to exist in multiple forms and be capable of ROS generation over multiple time periods, including one day, week or month, thus adding to the scope of their potential application.

In one embodiment, a composite comprising multiple layers of similar or dissimilar materials, such as porosity, is envisioned to achieve a desired thickness and wherein at least one of the layers is a nonwoven bioabsorbable semi-crystalline material. Suitable thickness of such a composite ranges from approximately 100 um to over approximately 10 mm. For instance, a more open pore layer can be on one side of the article to facilitate tissue ingrowth while a tighter pore layer is used on the opposite side to inhibit tissue ingrowth.

In addition, the materials of the present invention may be incorporated into any implantable medical device, such as stents, meshes, grafts, or any therapeutic composition. By "implantable medical device" is meant any object implanted through surgery, injection, placement, or application or other suitable means whose primary function is achieved either through its physical presence or mechanical properties.

EXAMPLES

Example 1

ROS Test Method of Detection Using the Pholasin® Assay

To determine the amount of ROS present in a particular sample a FLUOstar Omega multi-mode microplate reader (BMG Labtech Inc., Cary, N.C.) was utilized, typically with a 96-well sample plate. This reader has dual-syringe injector capacity, with the ability to inject reagents into sample wells. The protocol from ABEL assay kit 61M (Knight Scientific Ltd., 15 Wolseley Close Business Park, Plymouth, PL2 3BY, UK), which includes the ROS sensitive photoprotein Pholasin®, was followed for microplate parameters. The injector pumps were washed with reverse osmosis/deionized (RO/DI) water and the reader was set to the appropriate temperature (typically 37° C.).

In testing the polymeric samples, typically an approximately 0.5 cm diameter disc was used, which was slightly smaller than the diameter of a given well. Given the target number of samples to analyze, the appropriate numbers of wells were filled with a buffer solution, and then the polymeric discs were placed into the respective wells.

The sample well plate was quickly inserted into the microplate, and continuous photoluminescence measurements (reported in relative light units, or RLUs) were initiated and collected. After fifteen (15) minutes of equilibration, Pholasin® was injected or pipetted into each well containing a sample and the buffer solution. Data collection continued for an additional time period.

Example 2

Superoxide and Other ROS Determination Using the Pholasin® Assay

To determine the signal attributable to superoxide for a given sample, following the method described in Example 1, a sister sample well for the microplate was concurrently prepared in which the buffer was augmented additionally with superoxide dismutase (SOD). SOD was provided in the ABEL-61M test kit. The difference in normalized RLU traces between Example 1 and the sister well with SOD yielded the signal attributable to superoxide, typically reported as the maximum RLU. The "other ROS" that does not include superoxide is the data recorded for the sample well that contained SOD.

Example 3

Singlet Oxygen Test Method Using MCLA Assay on Microplate

A FLUOstar Omega multi-mode microplate reader was utilized, typically with a 96-well sample plate. Test chamber temperature was set to 37° C. In testing the polymeric samples, typically an approximately 0.5 cm diameter disc was used, which was slightly smaller than the diameter of a given well. The chemiluminescent indicator used to detect superoxide and singlet oxygen was MCLA, or 2-methyl-6-(p-methoxyphenyl)-3,7-(dihydroimidazo[1,2alpha]pyrazine-3-one (Bancirova, Luminescence, 26 (6), 685-88 (2011)). MCLA was purchased from Molecular Probes, Eugene, Oreg. Sister sample wells were prepared as follows:
  1. Irradiated coupon with buffered MCLA solution
  2. Irradiated coupon with buffered MCLA & SOD
  3. Irradiated coupon with buffered MCLA & SOD & $NaN_3$
  4. Irradiated coupon with buffered MCLA & $NaN_3$
  5. Buffered MCLA only Following well preparation, the well plate was quickly inserted into the microplate, and continuous photoluminescence measurements (reported in relative light units, or RLUs) were initiated and collected for about 5 minutes. The RLU difference between samples 1 and 2 is attributable to superoxide. The RLU difference between 1 and 4 is attributable to singlet oxygen. The RLU difference between 1 and 3 is attributable to superoxide and singlet oxygen. RLU from well 5 sets the control baseline.

Example 4

Modulated DSC Test Method

Modulated DSC (MDSC) was performed on a TA Instruments Q2000 DSC using the modulated DSC mode using the following setup:
initial sample heating from −50° C. to 250° C. using an underlying heating rate of 2° C./min. Modulation was carried out using a temperature range of +/−0.32° C. with a period of 60 seconds.

Example 5

Standard DSC Method

DSC was performed on a TA Instruments Q2000 DSC using the following setup:
initial sample heating from −50° C. to 300° C. at 10° C./min.

Example 6

HC Sample Preparation

Solid coupons of a given polymeric material were prepared via hot compressing pellets or powder as received from the supplier into solid sheets. Each was compressed for 5 minutes at 50 PSI and at a temperature appropriately at or above the melt as established through DSC. Samples were allowed to cool and then placed in a freezer at −20° C. for storage prior to irradiation. All coupons were irradiated at 45 kGy (Sterigenics—Corona, Calif.).

Example 7

EPR Test Method

EPR spectra were acquired with the Bruker Biospin X-band CW-EMX (Billerica, Mass.) spectrometer nominally operating at about 9 GHz with 100 kHz magnetic field modulation. Typically, spectra were acquired with a microwave power of less than 1 mW to avoid signal saturation, and multiple overlaying scans were run to arrive at an EPR spectrum.

Example 8

Crystalline and Amorphous EPR Results

Coupons of poly(d,l-lactic acid) (Polysciences Cat No 23976), poly(3-hydroxybutyrate) (Polysciences Cat No 16916), and poly(dioxanone) (Aldrich Cat No 719846) were prepared as in example 6. Coupons of poly(trimethlyene carbonate) (pTMC), and block copolymer of 2:1-PGA/TMC pellets were prepared in accordance with Example 6. Coupons were ambient-sealed in individual packages, and gamma-irradiated to a target of 45 kGy (Sterigenics—Corona, Calif.). Samples were maintained at room temperature. The time between irradiation and EPR measurement was approximately 8 weeks. For each irradiated sample, DSC was performed to detect the presence of a melt endotherm per Example (4 or 5). Similarly, to detect the presence of any stabilized free radicals, EPR was performed on each irradiated sample per Example 7. Results are tabulated Table 1.

TABLE 1

| DSC and EPR results | | |
|---|---|---|
| Material | Crystalline?* | Stabilized free radicals?** |
| poly(d,l-lactide) | No | No |
| poly(TMC) | No | No |
| P3OHB | Yes | Yes |
| 2:1 PGA:TMC | Yes | Yes |
| PDO | Yes | Yes |

*as determined by observation of a DSC melt peak
**as determined by observation of an EPR spectra Example 9

The free radical concentration of 45 kGy (target) irradiated of 2:1-PGA/TMC was measured as a function of temperature by EPR. The block copolymer of 2:1-PGA/TMC was prepared in accordance with U.S. Pat. No. 6,165,217. FIG. 3 shows the EPR signal decreasing with increasing temperature. As the temperature approaches the crystalline melt temperature (Tm approximately 200° C.) of this semi-crystalline polymer the EPR signal and, hence, the free radical concentration disappears. Once the free radicals disappear at 180° C., they do not reform upon cooling to room temperature as evidenced by the flat EPR response for the latter room temperature line in FIG. 3.

Example 10

The free radical concentration of 45 kGy irradiated of PDO was measured as a function of temperature by EPR. The semi-crystalline PDO polymer was ordered from Aldrich Cat No 719846. FIG. 7 shows the EPR signal decreasing with increasing temperature. As the temperature approaches the crystalline melt temperature (Tm approximately 110° C.) of this semi-crystalline polymer, the EPR signal and hence the free radical concentration disappears.

Example 11

The free radical concentration of a 45 kGy irradiated random block of 1:1-PGA/TMC was measured as a function of temperature by EPR. The pellet form of random block copolymer of 1:1-PGA/TMC was prepared in accordance with Example 6. FIG. 5 shows a very small EPR at room temperature. This small signal decreases with increasing temperature up to the crystalline melt temperature (Tm approximately 200° C.) of PGA. Subsequent measurement at room temperature shows even less EPR signal than with the initial unheated sample. This small EPR signal suggests the few free radicals present in the initial sample disappear upon heating to the PGA melt temperature and no free radicals form upon subsequent cooling to room temperature.

Example 12

The free radical concentration of 45 kGy irradiated of poly(3-hydroxybutyrate) (P3OHB) was measured as a function of temperature by EPR. The p3OHB was procured from Polysciences Cat No 16916. The sample was irradiated at 45 kGy and the EPR signal measured per Example 7. FIG. 8 shows a strong EPR signal at room temperature in response to the irradiated material having a relatively high free radical concentration. This free radical concentration and EPR signal then decreases with increasing temperature. As the temperature approaches the crystalline melt temperature (Tm approximately 170° C.) of this semi-crystalline polymer, the EPR signal and hence the free radical concentration disappears. Once the free radicals disappear at 180° C., they do not reform upon cooling to room temperature as evidenced by the flat EPR response for the latter room temperature line.

Example 13

Stability of Free Radicals Over Time

A 2:1-PGA/TMC was prepared in accordance with U.S. Pat. No. 6,165,217. The web was sealed in air/oxygen impermeable polymer packaging that included a dessicant pack (Minipak, Multisorb Technologies, Buffalo, N.Y.) to minimize uncontrolled, early hydrolysis of the polymer. The sample was then gamma-irradiated at a target dose of 25 kGy. From the large irradiated web sample, subsample coupons were to an approximately 2.5 cm×approximately 8 cm size. The initial weight of each coupon ranged between 1.5 and 1.8 g, as measured on a microbalance. Each coupon was placed in an individual 8 oz. screw-cap jar with approximately 250 ml of 3× phosphate buffered saline (PBS) (Sigma Chemical, P3813, St. Louis, Mo.). Jar lids were screw-sealed shut and placed in a heated circulating bath set to 37° C. Water bath level met or exceeded the water level in each sample jar.

Figure 11:
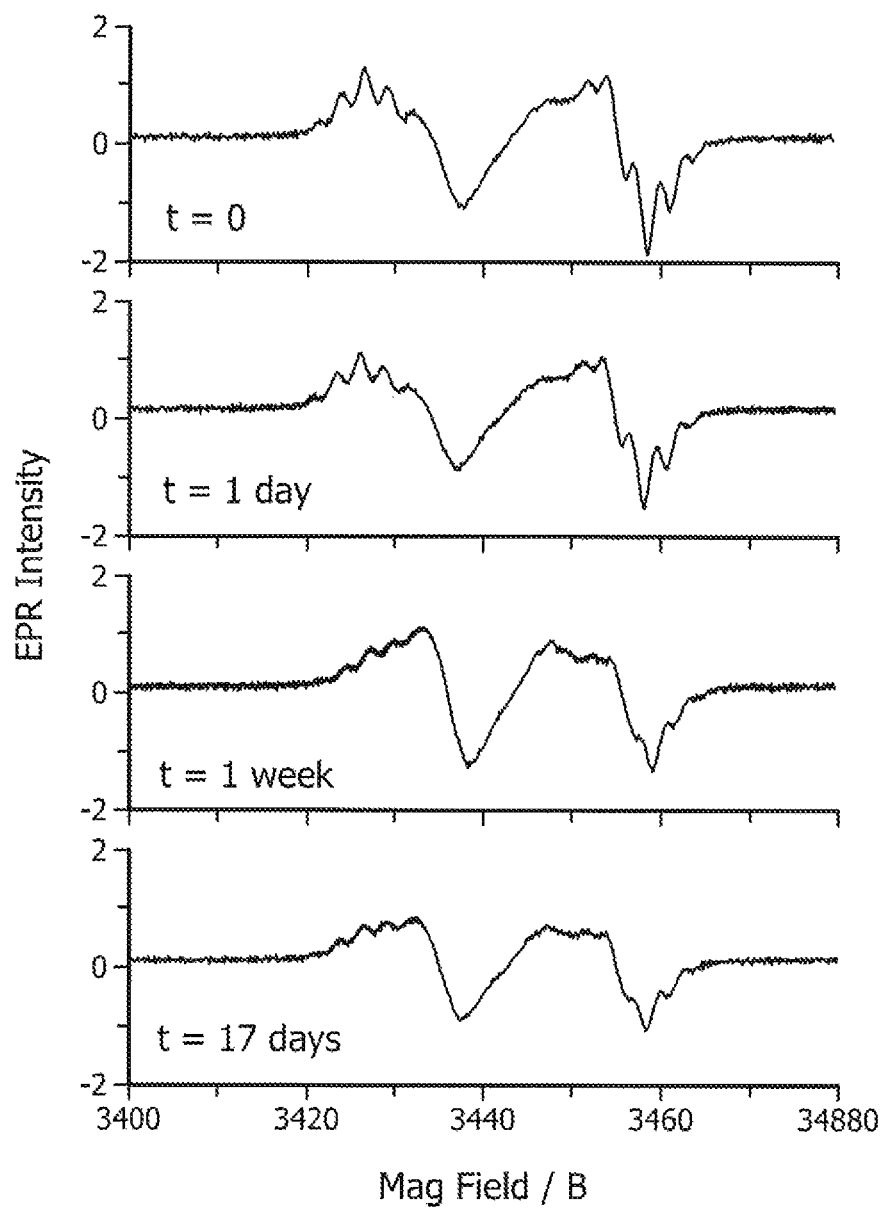
FIG. 11 shows EPR spectra of an irradiated sample of 2:1-PGA/TMC copolymer measured at various time points upon exposure to an oxygen containing aqueous media.

At select time periods, individual sample jars were removed and the sample removed from the jar. The sample was blotted dry on a fresh paper towel and weighed. The buffer-soaked sample was then transferred to an ambient vacuum chamber (no heating) and subjected to a high vacuum to remove residual water. Dryness was determined once a constant sample weight was achieved. This was observed to occur within 4-8 hours, though samples typically were held under vacuum overnight. Once dried, each sample was individually packaged in an impermeable barrier package with fresh desiccant. X-band EPR measurements at room temperature were performed on the irradiated, hydrolyzed samples as described in Example 7. An EPR response was measured at timepoints up to 17 days as shown in FIG. 11.

Example 14

ROS Over Time

A 2:1-PGA/TMC was prepared in accordance with U.S. Pat. No. 6,165,217. The web was sealed in air/oxygen impermeable polymer packaging that included a desiccant pack (Minipak, Multisorb Technologies, Buffalo, N.Y.) to minimize uncontrolled, early hydrolysis of the polymer. The sample was then gamma-irradiated at a target dose of 25 kGy. From the large irradiated web sample, subsample coupons were to an approximately 2.5 cm×approximately 8 cm size. The initial weight of each coupon ranged between 1.5 and 1.8 g, as measured on a microbalance. Each coupon was placed in an individual 8 oz. screw-cap jar with approximately 250 ml of 3× phosphate buffered saline (PBS) (Sigma Chemical, P3813, St. Louis, Mo.). Jar lids were screw-sealed shut and placed in a heated circulating bath set to 37° C. Water bath level met or exceeded the water level in each sample jar.

Figure 12:
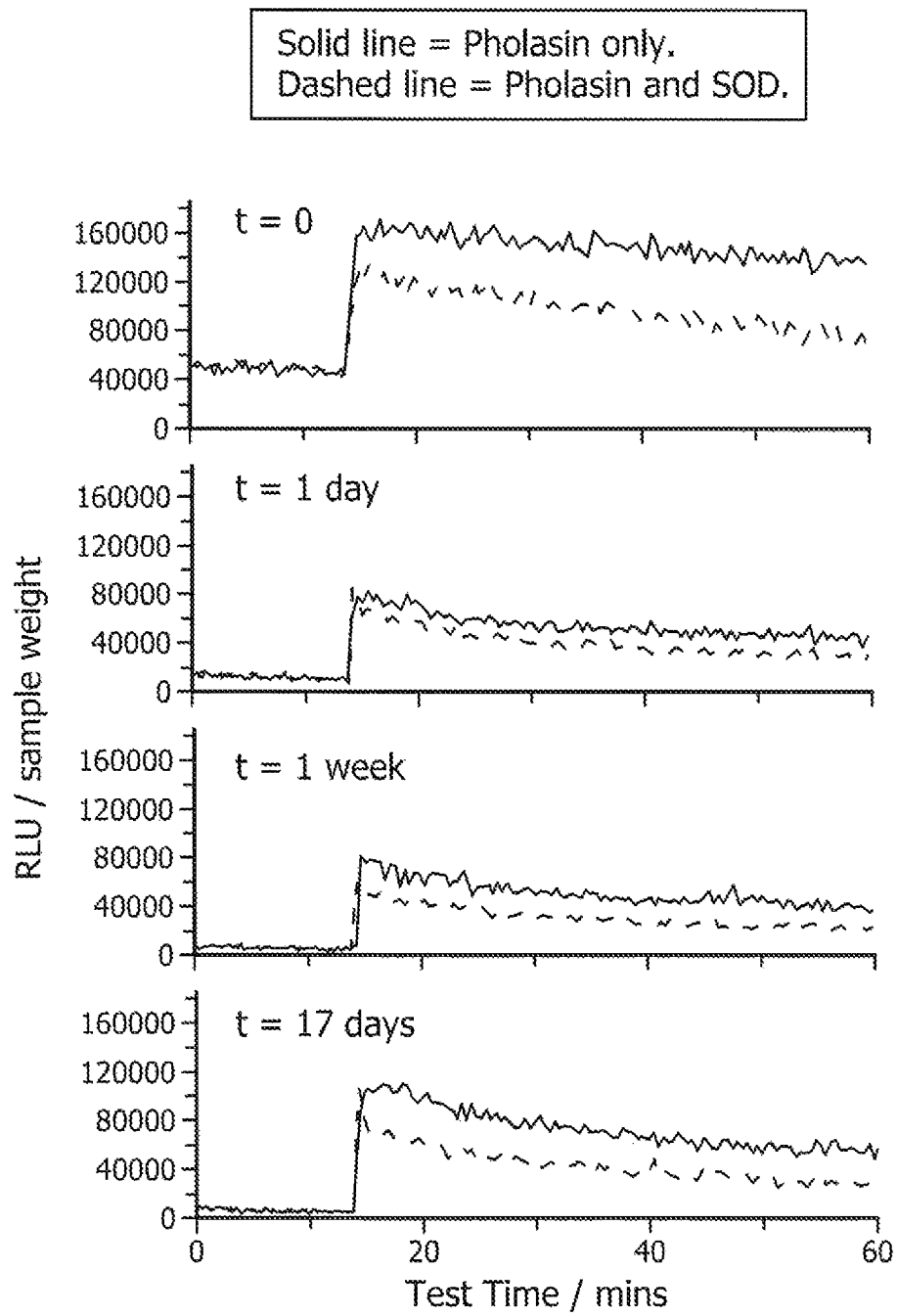
FIG. 12 is a graphical representation of continuous photoluminescence measurements reported in relative light units, or RLUs, which is an indicator of the presence of ROS in an irradiated 2:1-PGA/TMC copolymer web measured at various time points upon exposure to an oxygen containing aqueous media.

At select time periods, individual sample jars were removed and the sample removed from the jar. The sample was blotted dry on a fresh paper towel and weighed. The buffer-soaked sample was then transferred to an ambient vacuum chamber (no heating) and subjected to a high vacuum to remove residual water. Dryness was determined once a constant sample weight was achieved. This was observed to occur within 4-8 hrs, though samples typically were held under vacuum overnight. Once dried, each sample was individually packaged in an impermeable barrier package with fresh desiccant. ROS measurements were made on the irradiated, hydrolyzed samples as described in Example 1. ROS were detected at time points up to 17 days as shown in FIG. 12.

Example 15

Superoxide Over Time

A 2:1-PGA/TMC was prepared in accordance with U.S. Pat. No. 6,165,217. The web was sealed in air/oxygen impermeable polymer packaging that included a dessicant pack (Minipak, Multisorb Technologies, Buffalo, N.Y.) to minimize uncontrolled, early hydrolysis of the polymer. The sample was then gamma-irradiated at a target dose of 25 kGy. From the large irradiated web sample, subsample coupons were to an approximately 2.5 cm×approximately 8 cm size. The initial weight of each coupon ranged between 1.5 and 1.8 g, as measured on a microbalance. Each coupon was placed in an individual 8 oz. screw-cap jar with approximately 250 ml of 3× phosphate buffered saline (PBS) (Sigma Chemical, P3813, St. Louis, Mo.). Jar lids were screw-sealed shut and placed in a heated circulating bath set to 37° C. Water bath level met or exceeded the water level in each sample jar.

At select time periods, individual sample jars were removed and the sample removed from the jar. The sample was blotted dry on a fresh paper towel and weighed. The buffer-soaked sample was then transferred to an ambient vacuum chamber (no heating) and subjected to a high vacuum to remove residual water. Dryness was determined once a constant sample weight was achieved. This was observed to occur within 4-8 hours, though samples typically were held under vacuum overnight. Once dried, each sample was individually packaged in an impermeable barrier package with fresh desiccant. ROS measurements were made on irradiated, hydrolyzed samples as described in Examples 1 and 2. Superoxide was detected at timepoints up to 17 days as shown in FIG. 12.

Example 16

Amplex Red $H_2O_2$ Test Method

Sample solution for hydrogen peroxide ($H_2O_2$) determination was prepared by weighing test material and then placing into 500 µl phosphate-buffered-saline (PBS). Under a well-mixed condition at room temperature and after 30 minutes, 100 µl of the resultant supernatant was sampled.

The reaction solution was prepared freshly by mixing 50 µl of Amplex Red DMSO solution (Molecular Probes, Eugene, Oreg.), 100 μl of horseradish peroxidase solution (HRP, 10 unit/ml, Molecular Probes) and 4.85 ml of buffer solution. In a 96-well plate, 100 μl of supernatant was mixed with equal volume of reaction solution in each well and incubated at room temperature for 30 minutes. The fluorescence signal was then measured on a Fluostar Omega microplate reader at 540 nm/580 nm (excitation/emission). A sister sample well was prepared with approximately 700 U/ml catalase (from bovine liver, Sigma-Aldrich, cat. #C30). The RLU difference between the Amplex well and the Amplex well with catalase is attributable to hydrogen peroxide and was normalized by the weight of the sample used to prepare the sample solution.

Example 17

Temporal Release of Hydrogen Peroxide from Irradiated 2:1-PGA/TMC

A 2:1-PGA/TMC was prepared in accordance with U.S. Pat. No. 6,165,217. The web was sealed in air/oxygen impermeable polymer packaging that included a desiccant pack (Minipak, Multisorb Technologies, Buffalo, N.Y.) to minimize uncontrolled, early hydrolysis of the polymer. The sample was then gamma-irradiated at a target dose of 25 kGy. From the large irradiated web sample, subsample coupons were to an approximately 2.5 cm×approximately 8 cm size. The initial weight of each coupon ranged between 1.5 and 1.8 g, as measured on a microbalance. Each coupon was placed in an individual 8 oz. screw-cap jar with approximately 250 ml of 3× phosphate buffered saline (PBS) (Sigma Chemical, P3813, St. Louis, Mo.). Jar lids were screw-sealed shut and placed in a heated circulating bath set to 37° C. Water bath level met or exceeded the water level in each sample jar.

At select time periods, individual sample jars were removed and the sample removed from the jar. The sample was blotted dry on a fresh paper towel and weighed. The buffer-soaked sample was then transferred to an ambient vacuum chamber (no heating) and subjected to a high vacuum to remove residual water. Dryness was determined once a constant sample weight was achieved. This was observed to occur within 4-8 hrs, though samples typically were held under vacuum overnight. Once dried, each sample was individually packaged in an impermeable barrier package with fresh desiccant. $H_2O_2$ was detected on samples per Example 16 and reported on FIG. 13.

Example 17A

3 Month Release of Hydrogen Peroxide from Irradiated 2:1-PGA/TMC

A 2:1-PGA/TMC was prepared in accordance with U.S. Pat. No. 6,165,217. The web was sealed in air/oxygen impermeable polymer packaging that included a desiccant pack (Minipak, Multisorb Technologies, Buffalo, N.Y.) to minimize uncontrolled, early hydrolysis of the polymer. The sample was then gamma-irradiated at a target dose of 45 kGy. From the large irradiated web sample, subsample coupons were to an approximately 2.5 cm×approximately 8 cm size. The initial weight of each coupon was determined by a microbalance. Each coupon was placed in an individual screw-cap jar with approximately 250 ml of 3× phosphate buffered saline (PBS) (Sigma Chemical, P3813, St. Louis, Mo.). Jar lids were screw-sealed shut and placed in a heated circulating bath set to 37° C. Water bath level met or exceeded the water level in each sample jar.

At select time periods, individual sample jars were removed and the sample removed from the jar. The samples were dried. Once dried, each sample was individually packaged in an impermeable barrier package with fresh desiccant.

For hydrogen peroxide detection, a slightly modified method from Example 16 was followed. Sample solution for $H_2O_2$ was prepared by weighing test material and then placing into phosphate-buffered-saline (PBS) at a sample-weight-to-buffer-volume level of ~200 mg/mL. Under a well-mixed condition at room temperature and after 60 minutes, a subsample of the resultant supernatant was withdrawn.

The Amplex Red DMSO solution (Molecular Probes, Eugene, Oreg.) reaction solution was prepared. In a 96-well plate, the above supernatant was mixed with DMSO reaction solution in each well and incubated at 37° C. The fluorescence signal was then measured on a Fluostar Omega microplate reader at 540 nm/580 nm (excitation/emission). A sister sample well was prepared with approximately 100 U/ml catalase (from bovine liver, Sigma-Aldrich, cat. #C30). The RLU difference between the Amplex well and the Amplex well with catalase is attributable to hydrogen peroxide. The RLU signal was converted to absolute concentration of hydrogen peroxide by correlation to a calibration curve, created from diluted 3% stock hydrogen peroxide solutions.

Figure 13A:
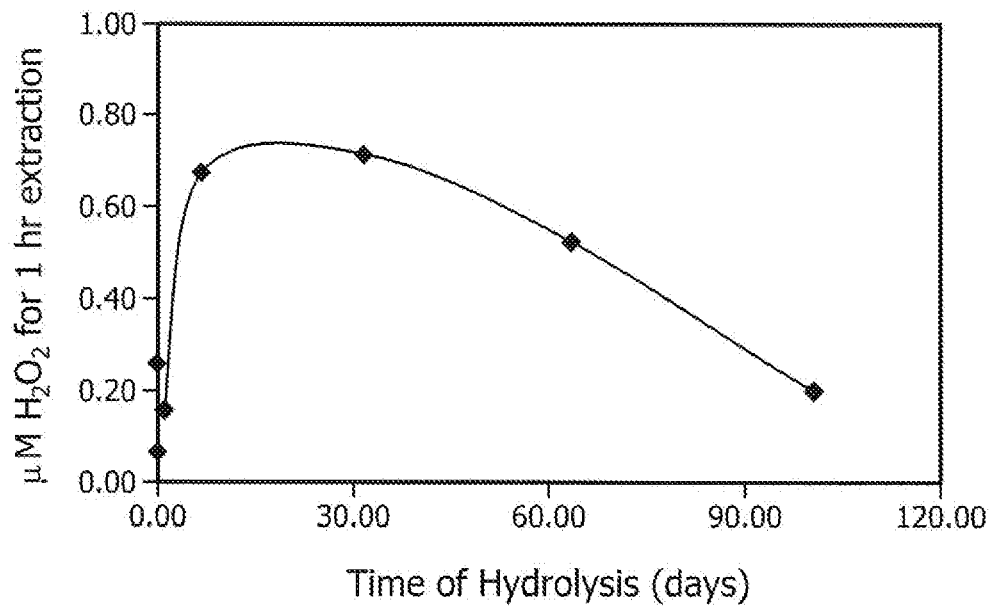
FIG. 13a is a graphical representation of hydrogen peroxide release from a sample of irradiated 2:1 PGA/TMC copolymer web measured over time.
Figure 13B:
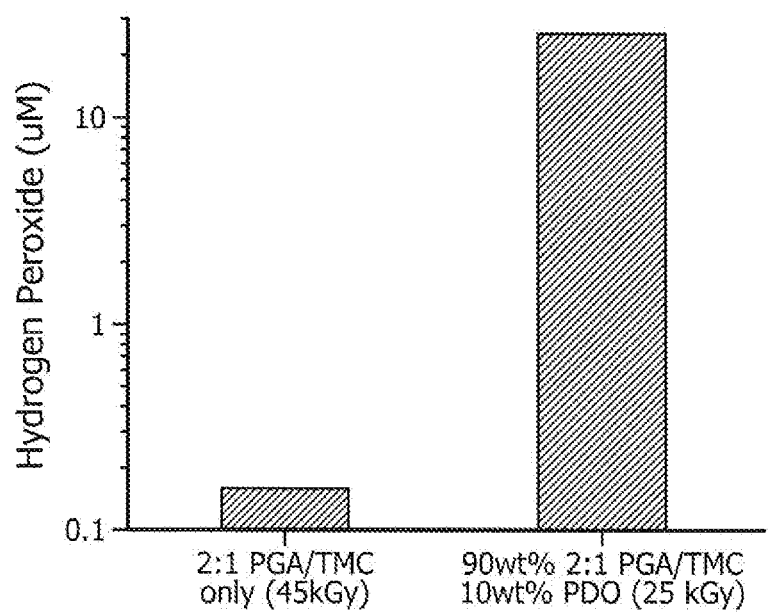
FIG. 13b is a graphical representation of the comparison of hydrogen peroxide release over time of an irradiated polymer granule blend comprised of 90 wt % 2:1-PGA/TMC and 10 wt % polydioxanone and an irradiated 2:1 PGA/TMC copolymer web.

For the hydrolyzed samples, hydrogen peroxide was detected greater than 3 months as reported in FIG. 13a.

Example 17B

Enhanced Hydrogen Peroxide Production with a Polymer Blend

A polymer granule blend comprised of 90 wt % 2:1-PGA/TMC and 10 wt % polydioxanone (PDO) (PDO purchased from Boehringer Ingelheim, lot#76013) was prepared in accordance with U.S. Pat. No. 6,165,217. Samples of web were sealed in air impermeable polymer packaging, including a desiccant pack (Minipak, Multisorb Technologies, Buffalo, N.Y.). The samples were irradiated at a target dose of 25 kGy. From a smaller subsample, hydrogen peroxide generation was determined per Example 16. The RLU signal was converted to absolute concentration of hydrogen peroxide by correlation to a calibration curve, created from diluted stock hydrogen peroxide solutions.

The signal for the blended sample above was compared to previous data from an unblended 2:1-PGA/TMC-only sample that was similarly prepared in accordance with U.S. Pat. No. 6,165,217, though was irradiated at a significantly higher target dose of 45 kGy. From a smaller subsample, hydrogen peroxide generation was determined per Example 16. The RLU signal was converted to absolute concentration of hydrogen peroxide by correlation to a calibration curve, created from diluted stock hydrogen peroxide solutions. As reported in FIG. 13b, the lower irradiated blend yielded a significantly higher amount of hydrogen peroxide than the unblended counterpart.

Example 18

Enhanced ROS, Inert Atmosphere Versus Air

A 2:1-PGA/TMC copolymer web was prepared in accordance with U.S. Pat. No. 6,165,217. Samples of web were sealed in air/oxygen impermeable polymer packaging, included a desiccant pack (Minipak, Multisorb Technologies, Buffalo, N.Y.). Immediately prior to package closure, ambient air in the package interior was removed by a dry nitrogen purge. Another sample package did not have the air purge prior to closure. The sealed packages were subsequently gamma-irradiated (Sterigenics, Corona, Calif.) at a 45 kGy target dose.

Figure 14:
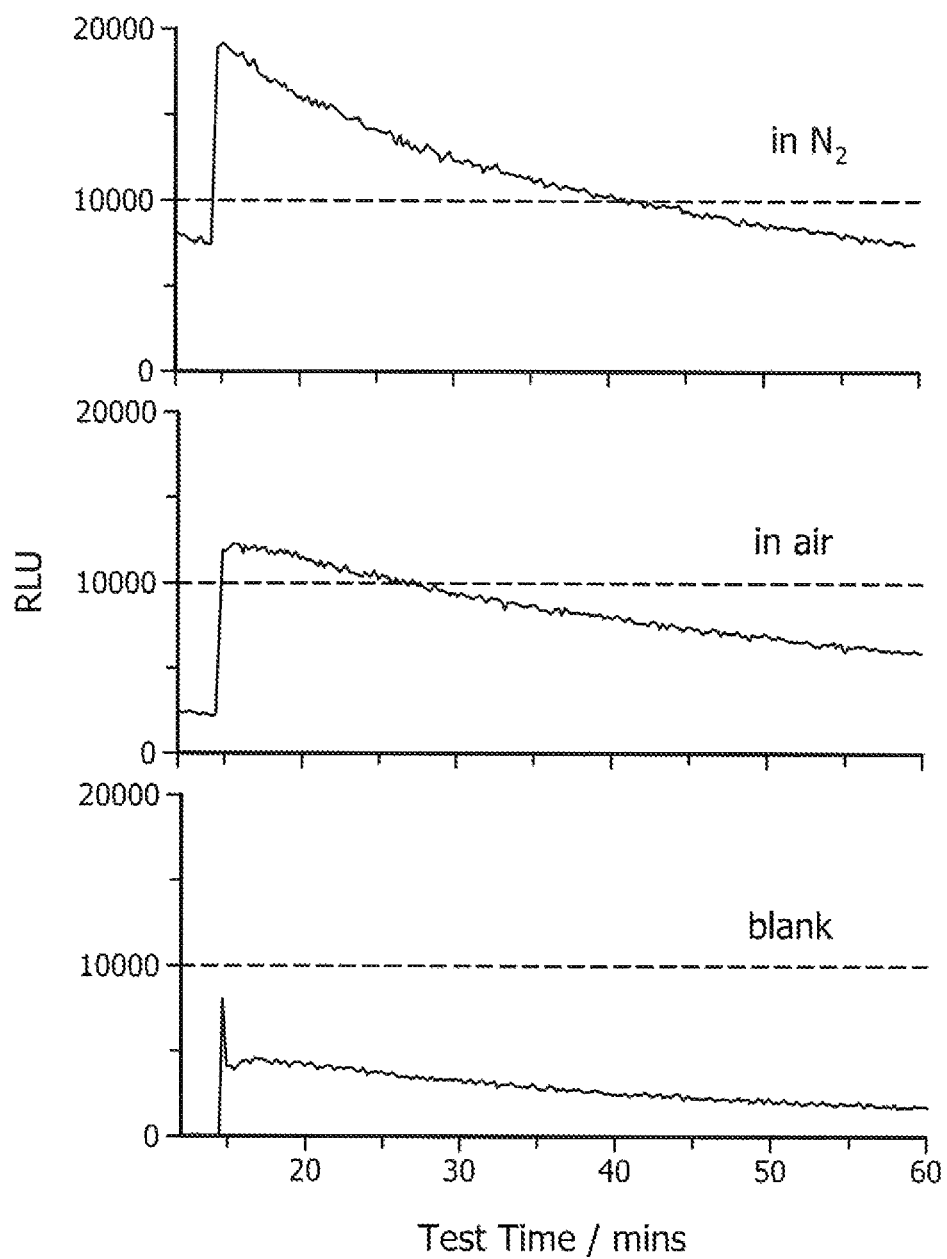
FIG. 14 shows a comparative representation of continuous photoluminescence measurements reported in RLUs indicating ROS content of samples of 2:1-PGA/TMC copolymer web irradiated under various atmospheric conditions.

Upon receipt, samples were removed and the Pholasin® assay was run as described in Example 1 to determine ROS signals. Superoxide amount was determined by Pholasin® assay as described in Example 2. Two samples were prepared per condition, and the average reported. The nitrogen atmosphere irradiated 2:1-PGA/TMC produced considerably higher ROS as estimated by Pholasin® assay than the air counterpart (see FIG. 14).

Example 19

Gamma Processing, EO Sterilized Example

Figure 15:
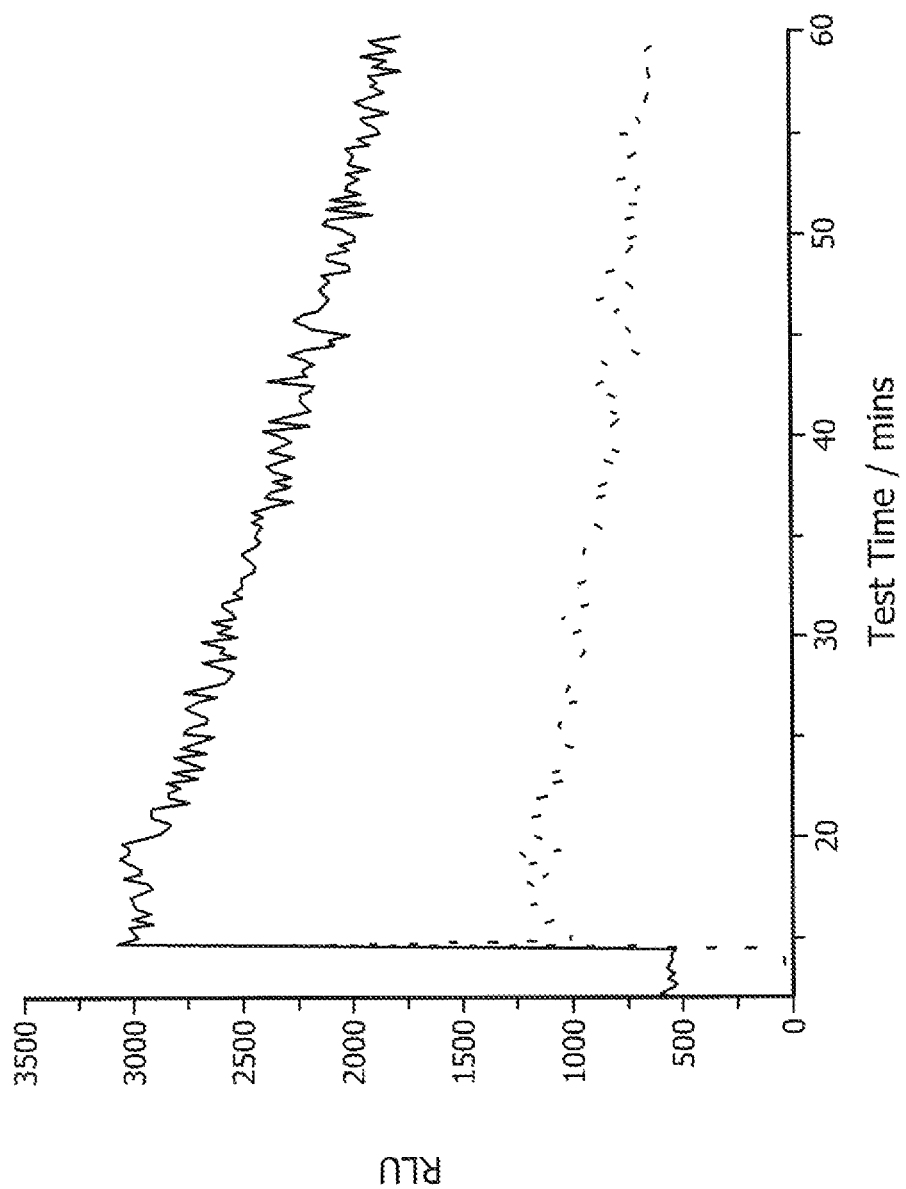
FIG. 15 is a graphical representation of continuous photoluminescence measurements reported in RLUs indicating ROS content in a 2:1-PGA/TMC copolymer web that has been gamma irradiated and subsequently exposed to ethylene oxide (EO) sterilization.
Figure 16:
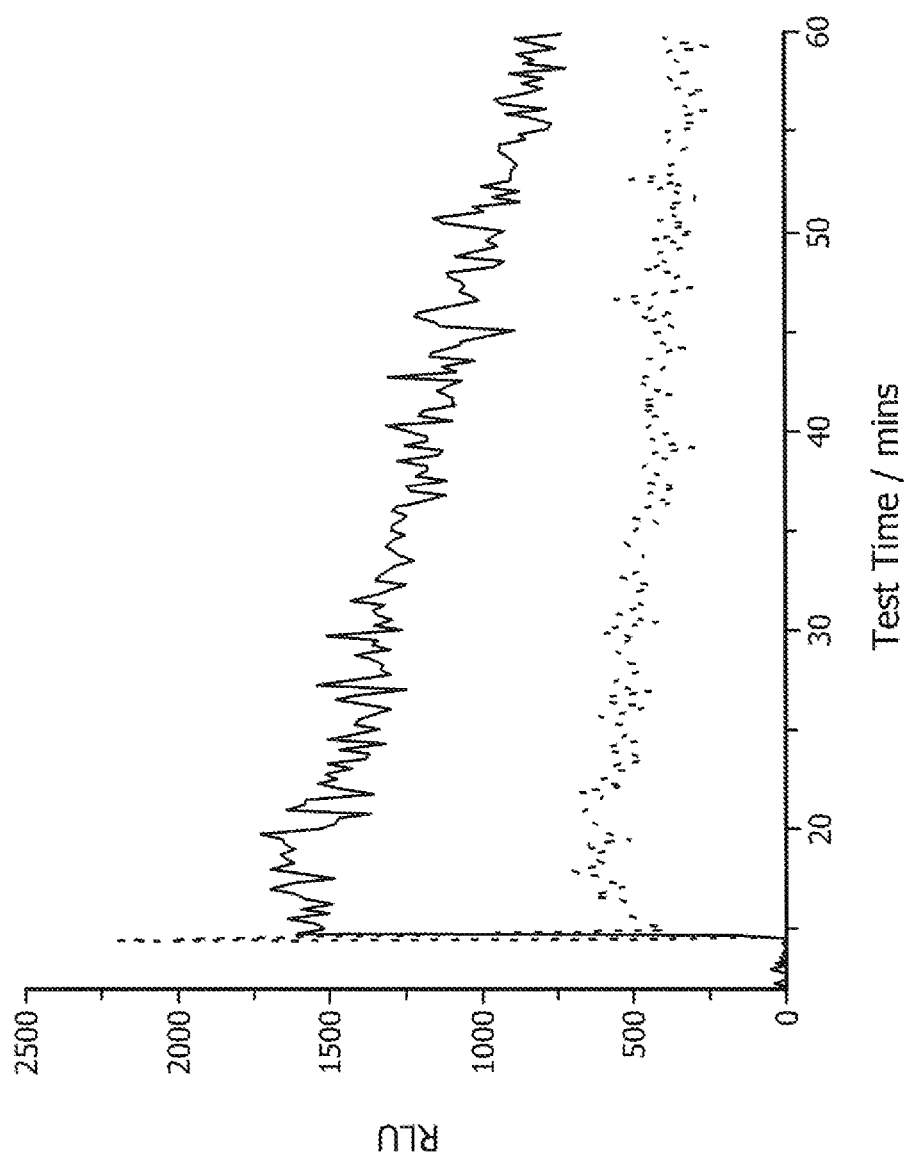
FIG. 16 is a graphical representation of the superoxide content of the 2:1-PGA/TMC web of FIG. 15 over time.

A 2:1-PGA/TMC copolymer web was prepared in accordance of U.S. Pat. No. 6,165,217 and subjected to a target 20 kGy gamma irradiation (Sterigenics, Corona, Calif.) and subsequent ethylene oxide sterilization (Sterilization Services, Atlanta, Ga. 30336) and tested per Examples 1 and 2. Two samples were prepared per condition, and the average reported. The sample produced ROS as shown in FIG. 15, including superoxide as shown in FIG. 6, as evidenced by the higher peak at approximately 20 minutes compared to the blank control sample.

Example 20

Low Surface Area (HC'd) Embodiment with ROS

Figure 17:
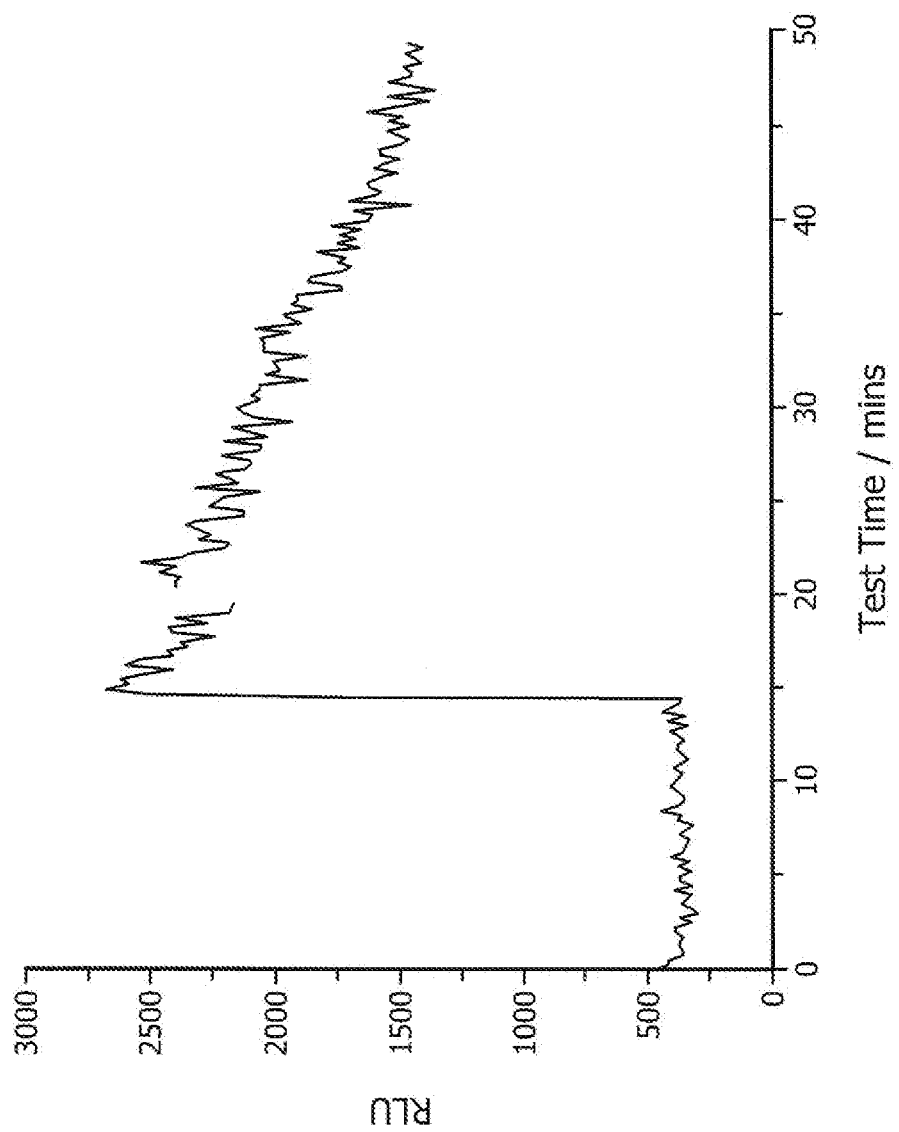
FIG. 17 is a graphical representation of continuous photoluminescence measurements reported in RLUs indicating ROS content in an irradiated 2:1-PGA/TMC copolymer in solid coupon form.

2:1-PGA/TMC block copolymer solid coupons were prepared from material in accordance to U.S. Pat. No. 4,243,775 and processed per Example 6 of this document. The surface area of this material was calculated to be approximately 0.002 $m^2$/gm based on the geometry of the compressed disk that was subsequently used for the ROS determination. ROS determination was carried out following Example 1 of this document as shown in FIG. 17.

Example 21

High Surface Area, Electrospun 2:1-PGA/TMC

Figure 18:
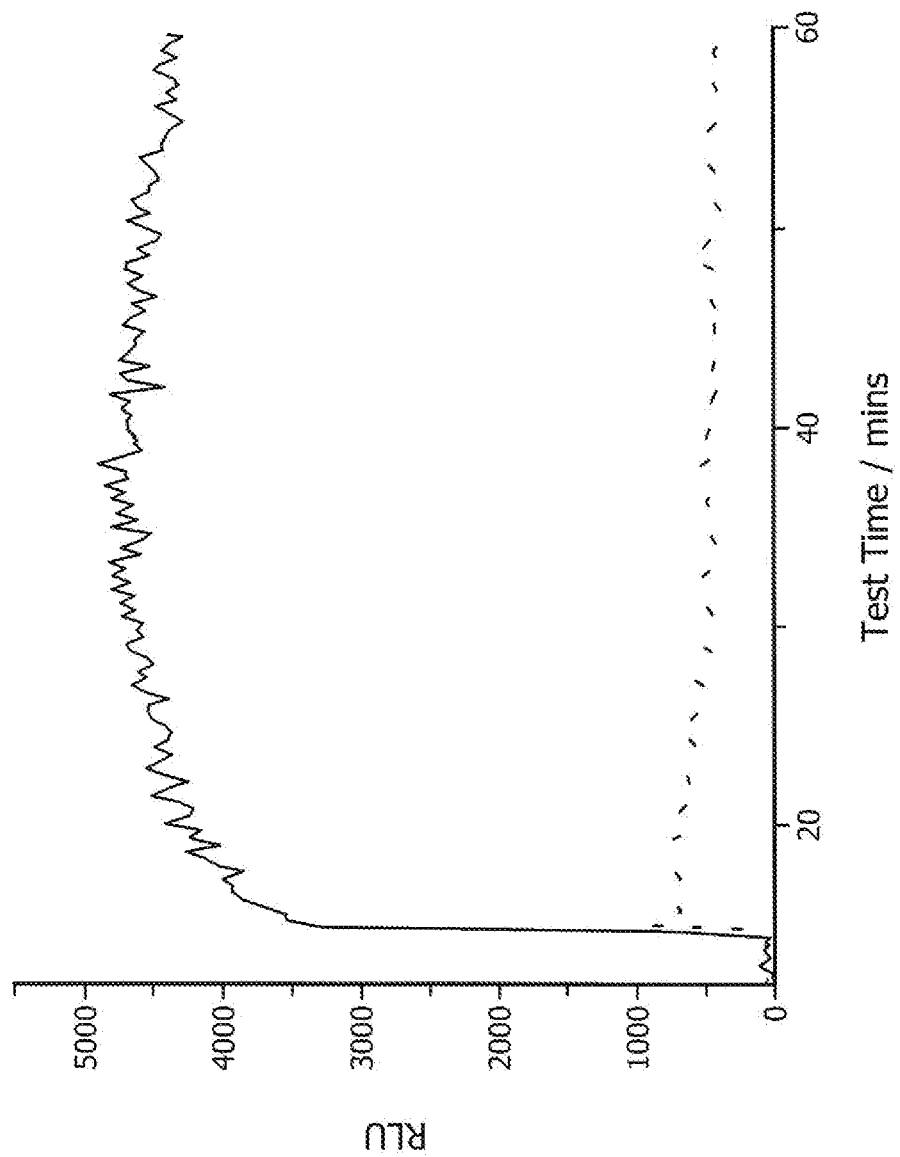
FIG. 18 is a graphical representation of superoxide content at various time points upon exposure to an oxygen containing aqueous media over time of an electrospun form of irradiated 2:1-PGA/TMC copolymer.

The superoxide generated by electrospun form of 45 kGy gamma irradiated 2:1-PGA/TMC was measured as a function of time using the Pholasin assay method. A four-layer electrospun sample was prepared from a solution of 4% weight 2:1-PGA/TMC in hexafluoro-2-propanol (HFIP). An Elmarco NS Lab 500 electrospinning unit was used to spin fibers from this solution followed by 5 minutes at 120° C. to cold crystallize. A first layer was produced by electrospinning a thin layer of 2:1-PGA/TMC nanofibers onto a metal plate. To increase the layer thickness, additional solution was added and three additional layers of electrospun 2:1-PGA/TMC fibers deposited. The resulting sample was comprised of a total of four electrospun layers. The fiber diameter ranged from below 100 nm to greater than approximately 1.5 microns. Each sample was irradiated using e-beam at a dose of 45 kGy (Sterigenics, Corona, Calif.) Tested per Example 2 and the results shown in FIG. 18. The specific surface area of this material was measured by BET and found to be approximately 4.3 $m^2$/gm.

Example 22

Singlet Oxygen Detection on Irradiated Material

Figure 19:
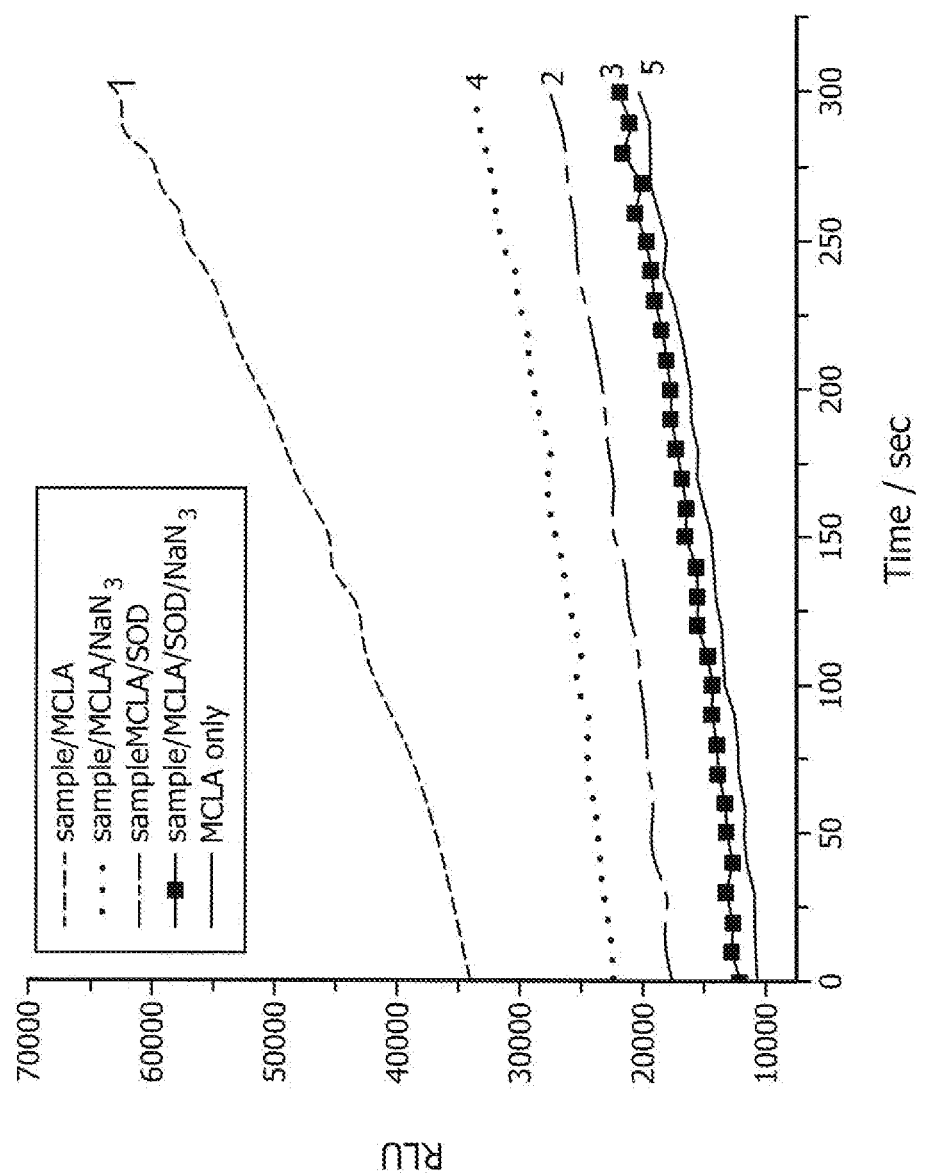
FIG. 19 is a graphical representation of continuous photoluminescence measurements reported in RLUs of irradiated 2:1-PGA/TMC copolymer samples. Differences between sample measurements indicate the level of singlet oxygen and superoxide generated by the samples upon exposure to an oxygen containing aqueous media.
Figure 20:
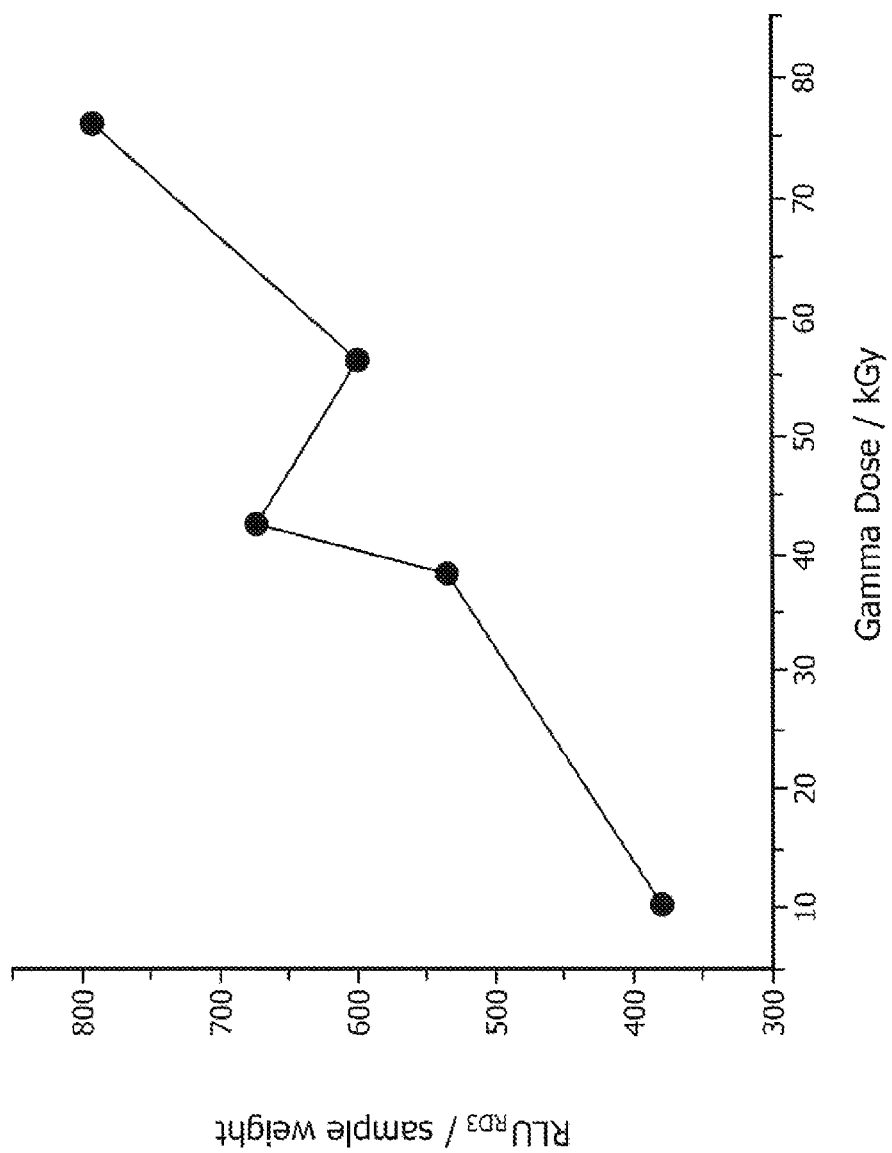
FIG. 20 is a graphical representation of continuous photoluminescence measurements reported in RLUs indicating ROS content in 2:1 PGA/TMC copolymer samples at various irradiation dose levels.
Figure 21A:
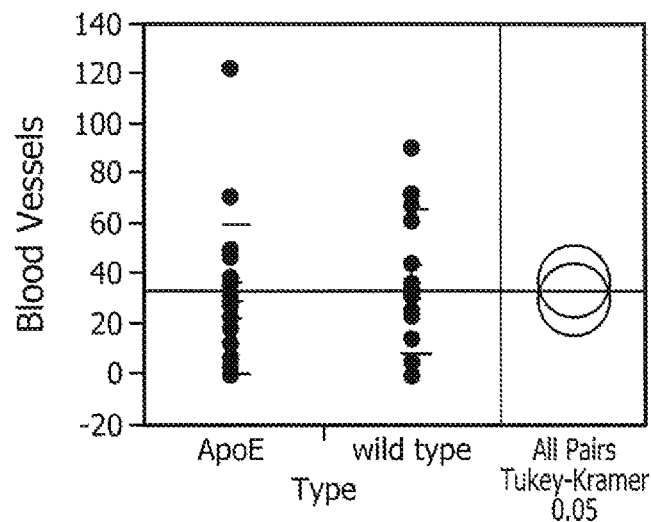
FIGS. 21a and 21b are graphical representations of a JMP Version 10.2.2 (SAS Institute) Oneway Analysis of Blood Vessels for Group A in Example 23 for 7 days and 14 days, respectively.
Figure 21B:
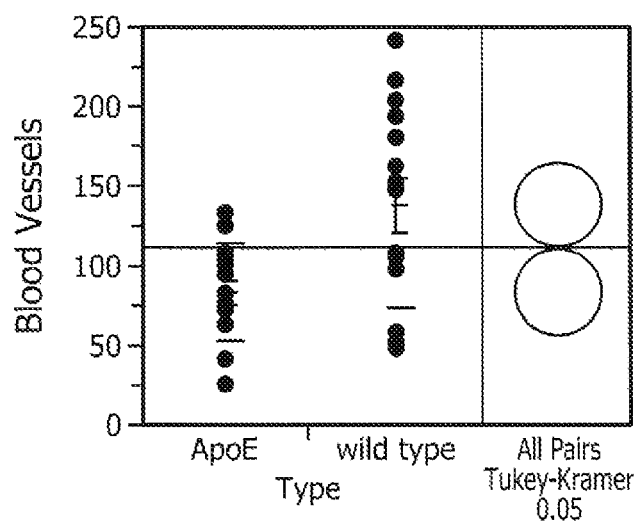
Figure 22A:
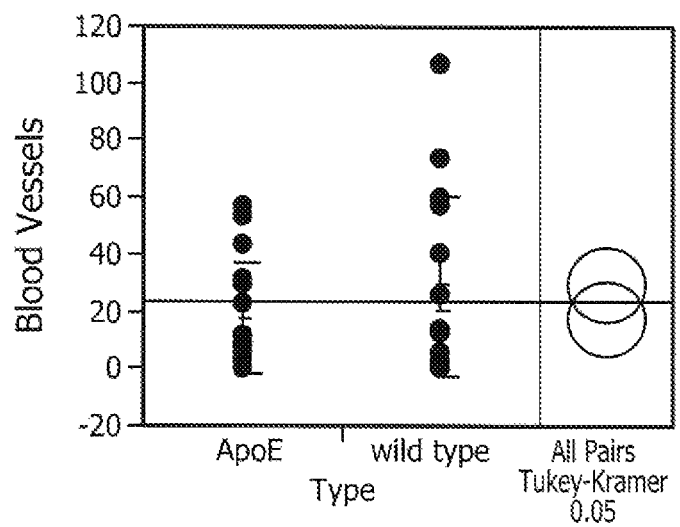
FIGS. 22a and 22b are graphical representations of a JMP Version 10.2.2 (SAS Institute) Oneway Analysis of Blood Vessels for Group B in Example 23 for 7 days and 14 days, respectively.
Figure 22B:
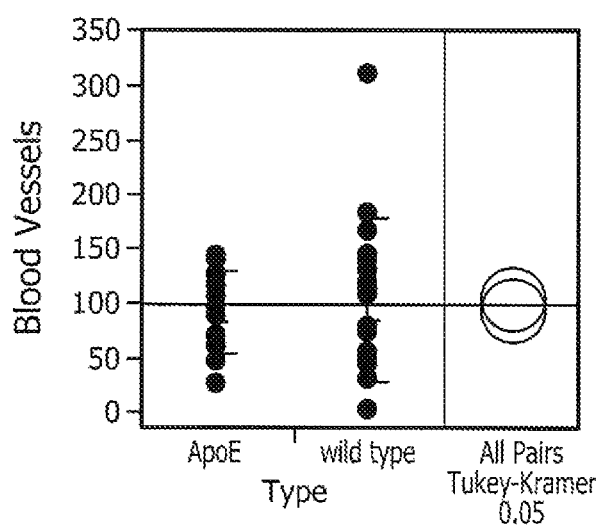

A 2:1-PGA/TMC was prepared in accordance with U.S. Pat. No. 6,165,217. The web was sealed in air/oxygen impermeable polymer packaging that included a desiccant pack (Minipak, Multisorb Technologies, Buffalo, N.Y.) to minimize uncontrolled, early hydrolysis of the polymer. The sample was then gamma-irradiated at a target gamma dose of 45 kGy. Coupons of the irradiated material were tested per Example 3. Signals attributable to both superoxide and singlet oxygen were determined as shown in FIG. 19.

Example 23

Comparison of Irradiated and Non-Irradiated Material on Blood Vessel Formation

Ethylene oxide sterilized, non-irradiated semi-crystalline hydrolytically degradable polymeric material (Group A) was prepared as follows. A 2:1-PGA/TMC copolymer web was prepared in accordance of U.S. Pat. No. 6,165,217, vacuum dried at 120° C. overnight, packaged in air/oxygen impermeable polymer packaging that included a desiccant pack (Minipak, Multisorb Technologies, Buffalo, N.Y.) to minimize uncontrolled, early hydrolysis of the polymer. Nominally 1 cm web discs were cut from the web and then repackaged into air/oxygen impermeable polymer packaging that included a desiccant pack (Minipak, Multisorb Technologies, Buffalo, N.Y.). To sterilize the coupons, they were transferred in ethylene oxide (EO) permeable packaging and subjected to an ethylene oxide exposure sufficient for sterilization (300 minutes EO exposure) (Nelson Labs, Salt Lake City, Utah). The material was received and repacked into air/oxygen impermeable polymer packaging that included a desiccant pack (Minipak, Multisorb Technologies, Buffalo, N.Y.) until needed for further use.

Gamma irradiated semi-crystalline hydrolytically degradable polymeric material (Group B) was prepared as follows. A 2:1-PGA/TMC copolymer web was prepared in accordance of U.S. Pat. No. 6,165,217, vacuum dried at 120 C overnight, packaged in air/oxygen impermeable polymer packaging that included a desiccant pack (Minipak, Multisorb Technologies, Buffalo, N.Y.) to minimize uncontrolled, early hydrolysis of the polymer. Nominally 1 cm web discs were cut from the web and then repackaged into air/oxygen impermeable polymer packaging that included a desiccant pack (Minipak, Multisorb Technologies, Buffalo, N.Y.). The discs were then irradiated to a (nominal) target of 45 kGy gamma irradiation (Sterigenics, Corona, Calif.) and the package remained unopened until needed for further use.

For the purpose of evaluating the angiogenic effect of a ROS-generating device in-vivo, the apoE −/− mouse model was selected as it has been shown to exhibit impaired blood vessel development compared to the C57-wild-type analog (Couffinhal et al., Circulation, 99, 3188-98 (1999)), and become a widely-used pre-clinical model to study angiogenesis (Silva et al., Biomaterials, 31(6), 1235-41 (2010)). Sterile discs from Group A and Group B were used as treatment groups in this study, thereby comparing the effect of ROS generating material of identical form.

One disc from each treatment group was subcutaneously implanted into the left and right dorsum of ApoE−/− mice and wild-type controls. Inlife timepoints were 3, 7, and 14 days. Six mice of each type were dedicated to each timepoint. After sacrifice, each implant was removed and fixed en bloc and transferred to the histology lab. Three cross-sections per disc were processed and stained with H&E (hematoxylin and eosin) and CD31 antibody. Each cross section was then manually assessed by an experienced histologist for blood vessel counts within the margins of the implant under 100× optical magnification and the data were analyzed by JMP version 10.2.2 (SAS Institute, Cary, N.C.). No blood vessels were observed amongst all 3 day implants. Blood vessels were counted at days 7 and 14 amongst both conditions and mouse types.

In comparing Group A there was an insignificant difference in blood vessel count seen in the apoE−/− mouse versus the wild-type mouse at day 7. However, this blood vessel count difference reached statistical significance at day 14 as demonstrated below, with the blood vessel count of the apoE−/− mice being lower than that of the wild type mice.

TABLE 2

Means and Standard Deviations

| (Group A, day 7) | | | | (Group A, day 14) | | | |
|---|---|---|---|---|---|---|---|
| Group | N | Mean | Std Dev | Group | n | Mean | Std Dev |
| ApoE | 18 | 29.9444 | 29.9086 | ApoE | 15 | 84.400 | 30.2792 |
| wild type | 18 | 37.2222 | 29.1539 | wild type | 16 | 138.938 | 64.1347 |

TABLE 3

LSD Threshold Matrix
Positive values show pairs of means that are significantly different

| (Group A, day 7) | | | (Group A, day 14) | | |
|---|---|---|---|---|---|
| Abs(Dif)-HSD | wild type | ApoE | Abs(Dif)-HSD | wild type | ApoE |
| wild type | −20.007 | −12.729 | wild type | −36.659 | 17.273 |
| ApoE | −12.729 | −20.007 | ApoE | 17.273 | −37.861 |

TABLE 4

Levene Test
Variance equivalence between groups p < 0.05 show variances are unequal

| (Group A, day 7) | | | | (Group A, day 14) | | | |
|---|---|---|---|---|---|---|---|
| Test | F Ratio | DFNum | DFDen | p-Value | Test | F Ratio | DFNum | DFDen | p-Value |
| Levene | 0.1602 | 1 | 34 | 0.6915 | Levene | 12.8584 | 1 | 29 | 0.0012* |

TABLE 5

Welch's Test
Anova testing means equal, allowing standard deviations not equal, prob < 0.05 shows that groups are statistically not equal

| | (Group A, day 14) | | | | |
|---|---|---|---|---|---|
| (Group A, day 7) | F Ratio | DFNum | DFDen | t Test | Prob > F |
| n/a | 9.3474 | 1 | 21.668 | 3.0573 | 0.0058* |

In the ROS-generating Group B, there was a statistically insignificant difference in blood vessel count between the apoE−/− and wild-type mice at both day 7 and day 14, as demonstrated below. This seems to indicate that the presence of the ROS generating Group B material in the apoE−/− mice negated the difference in blood vessel counts as compared to wild-type mice.

TABLE 6

Means and Standard Deviations

| (Group B, day 7) | | | | (Group B, day 14) | | | |
|---|---|---|---|---|---|---|---|
| Level | n | Mean | Std Dev | Level | n | Mean | Std Dev |
| ApoE | 16 | 18.1250 | 19.3800 | ApoE | 17 | 92.941 | 37.7814 |
| wild type | 16 | 29.4375 | 31.7825 | wild type | 17 | 103.824 | 74.3297 |

TABLE 7

LSD Threshold Matrix
Positive values show pairs of means that are significantly different

| (Group B, day 7) | | | Group B, day 14 | | |
|---|---|---|---|---|---|
| Abs(Dif)-HSD | wild type | ApoE | Abs(Dif)-HSD | wild type | ApoE |
| wild type | −19.006 | −7.694 | wild type | −41.193 | −30.310 |
| ApoE | −7.694 | −19.006 | ApoE | −30.310 | −41.193 |

TABLE 8

Levene Test
variance equivalence between groups
p < 0.05 show variances are unequal

| | (Group B, day 7) | | | | | (Group B, day 14) | | | |
|---|---|---|---|---|---|---|---|---|---|
| Test | F Ratio | DFNum | DFDen | p-Value | Test | F Ratio | DFNum | DFDen | p-Value |
| Levene | 3.3766 | 1 | 30 | 0.0761 | Levene | 3.6995 | 1 | 32 | 0.0634 |

TABLE 9

Welch's Test
Anova testing Means Equal, allowing Std Devs Not Equal,
prob < 0.05 shows that groupsare statistically not equal

| (Group B, day 7) | (Group B, day 14) |
|---|---|
| n/a | n/a |

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. A biocompatible device capable of releasing superoxide comprising:
   a substrate; and
   a biocompatible material comprising at least one semi-crystalline, hydrolytically degradable polymeric material, the polymeric material having been subjected to ionizing radiation at a dose rate less than about 50 kGy and sterilized by non-ionizing radiation methods; said polymeric material being in contact with at least a portion of said substrate,
   wherein said at least one semi-crystalline, hydrolytically degradable polymeric material comprises a first polymeric material and a second polymeric material,
   wherein at least one of said first and second polymeric materials comprises stabilized free radicals;
   wherein said first polymeric material and said second polymeric material have been subjected to different doses of ionizing radiation, and
   wherein the biocompatible material, upon contact with aqueous media, enable multi-phasic generation of reactive oxidative species.

2. A biocompatible device capable of releasing superoxide comprising:
   a substrate; and
   a biocompatible material comprising at least one semi-crystalline, hydrolytically degradable polymeric material, the polymeric material having been subjected to ionizing radiation while maintained in an inert atmosphere; said polymeric material being in contact with at least a portion of said substrate,
   wherein said at least one semi-crystalline, hydrolytically, degradable polymeric material comprises a first polymeric material and a second polymeric material,
   wherein at least one of said first and second polymeric materials comprises stabilized free radicals;
   wherein said first polymeric material and said second polymeric material have been subjected to different doses of ionizing radiation, and
   wherein the biocompatible material, upon contact with aqueous media, enable multi-phasic generation of reactive oxidative species.

3. The biocompatible device of claim 1, wherein the first polymeric material has a different hydrolytic degradation rate than the second polymeric material.

4. The biocompatible device of claim 1, wherein the first polymeric material has a different degree of crystallinity than the second polymeric material.

5. The biocompatible device of claim 1, wherein the first polymeric material comprises a different amount of stabilized free radicals than the second polymeric material.

6. The biocompatible device of claim 1, wherein at least one of said first and second polymeric materials is bioabsorbable.

7. The biocompatible device of claim 6, wherein the bioabsorbable polymer is selected from the group consisting of poly(dioxanone), poly(glycolide), poly(lactide) poly($\epsilon$-caprolactone), poly(anhydrides) such as poly(sebacic acid), poly(hydroxyalkanoates) such as poly(3-hydroxybutyrate), copolymers of any of these and combinations thereof.

8. The biocompatible device of claim 2, wherein the first polymeric material has a different hydrolytic degradation rate than the second polymeric material.

9. The biocompatible device of claim 2, wherein the first polymeric material has a different degree of crystallinity than the second polymeric material.

10. The biocompatible device of claim 2, wherein the first polymeric material comprises a different amount of stabilized free radicals than the second polymeric material.

11. The biocompatible device of claim 2, wherein at least one of said first and second polymeric materials is bioabsorbable.

12. The biocompatible device of claim 11, wherein the bioabsorbable polymer is selected from the group consisting of poly(dioxanone), poly(glycolide), poly(lactide) poly($\epsilon$-caprolactone), poly(anhydrides) such as poly(sebacic acid), poly(hydroxyalkanoates) such as poly(3-hydroxybutyrate), copolymers of any of these and combinations thereof.

* * * * *